(12) United States Patent
Sendai

(10) Patent No.: US 7,283,858 B2
(45) Date of Patent: *Oct. 16, 2007

(54) FLUORESCENT-LIGHT IMAGE DISPLAY METHOD AND APPARATUS THEREFOR

(75) Inventor: Tomonari Sendai, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 576 days.

This patent is subject to a terminal disclaimer.

(21) Appl. No.: 09/874,355

(22) Filed: Jun. 6, 2001

(65) Prior Publication Data

US 2002/0105505 A1    Aug. 8, 2002

(30) Foreign Application Priority Data

Jun. 6, 2000  (JP) .............................. 2000-169196
Sep. 26, 2000  (JP) .............................. 2000-291721

(51) Int. Cl.
    *A61B 5/00*   (2006.01)
(52) U.S. Cl. ...................... 600/407; 600/476; 600/478; 600/160
(58) Field of Classification Search ................ 600/473, 600/160, 475–478, 407, 178, 180; 345/77, 345/589; 348/65, 77; 250/458.1, 461.1; 382/274

See application file for complete search history.

(56) References Cited

U.S. PATENT DOCUMENTS

| | | | |
|---|---|---|---|
| 5,647,368 A * | 7/1997 | Zeng et al. ................. | 600/476 |
| 5,749,830 A | 5/1998 | Kaneko et al. | |
| 5,769,792 A | 6/1998 | Palcic et al. | |
| 6,002,137 A | 12/1999 | Hayashi | |
| 6,236,881 B1 * | 5/2001 | Zahler et al. ............... | 600/476 |
| 6,293,911 B1 * | 9/2001 | Imaizumi et al. ........... | 600/160 |
| 6,422,994 B1 * | 7/2002 | Kaneko et al. ............. | 600/160 |
| 6,433,345 B1 * | 8/2002 | Hayashi et al. .......... | 250/458.1 |
| 2002/0085753 A1 * | 7/2002 | Sendai ....................... | 382/168 |
| 2002/0138008 A1 * | 9/2002 | Tsujita et al. ............... | 600/473 |
| 2002/0177780 A1 * | 11/2002 | Sendai ....................... | 600/476 |
| 2003/0013937 A1 * | 1/2003 | Tsujita et al. ............... | 600/109 |
| 2003/0055341 A1 * | 3/2003 | Banerjee ..................... | 600/476 |
| 2003/0078477 A1 * | 4/2003 | Kang et al. ................. | 600/178 |
| 2003/0135092 A1 * | 7/2003 | Cline et al. ................. | 600/160 |
| 2003/0153825 A1 * | 8/2003 | Mooradian et al. ......... | 600/407 |
| 2003/0191368 A1 * | 10/2003 | Wang et al. ................ | 600/160 |
| 2004/0044275 A1 * | 3/2004 | Hakamata ................... | 600/310 |

FOREIGN PATENT DOCUMENTS

EP           0 920 831 A1    6/1999

* cited by examiner

*Primary Examiner*—Ruth S. Smith
(74) *Attorney, Agent, or Firm*—Sughrue Mion, PLLC

(57) ABSTRACT

An image containing data relating to the tissue-state and the tissue-form of a target area is displayed. A fluorescent-light image having two different wavelength bands of fluorescent-light is obtained, based on the strength of the fluorescent light emitted from a target area irradiated by stimulating-light. A reflected-light image is obtained based on the strength of the light reflected from a target area irradiated by white-light as reference-light. A hue is assigned to a computed-image based on a division value of each pixel value of aforementioned fluorescent-light image to form a tissue-state image reflecting mainly the tissue-state, and a brightness is assigned to the reflected-light image to form a tissue-form image reflecting mainly the tissue-form. The tissue-state image and the tissue-form image are combined to form a composite-image, and the composite-image is displayed.

42 Claims, 21 Drawing Sheets

F I G . 1
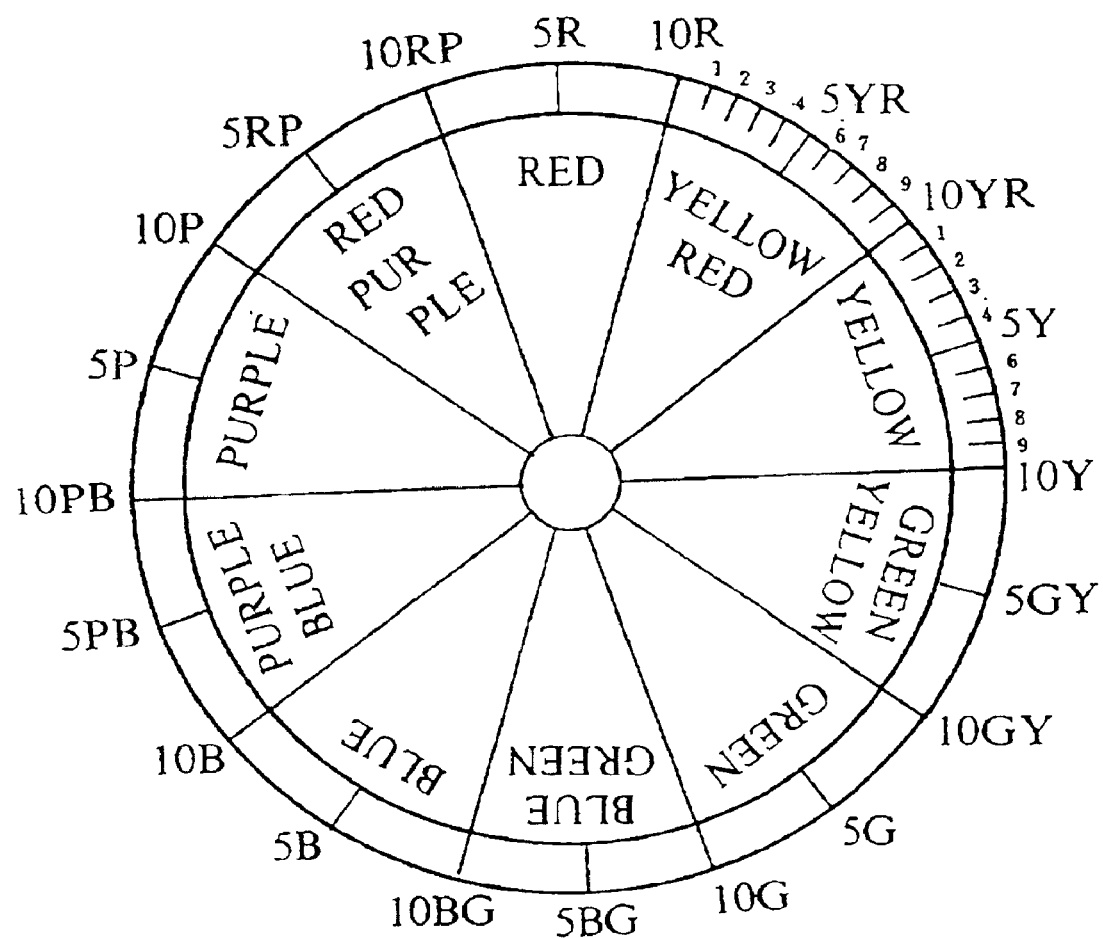

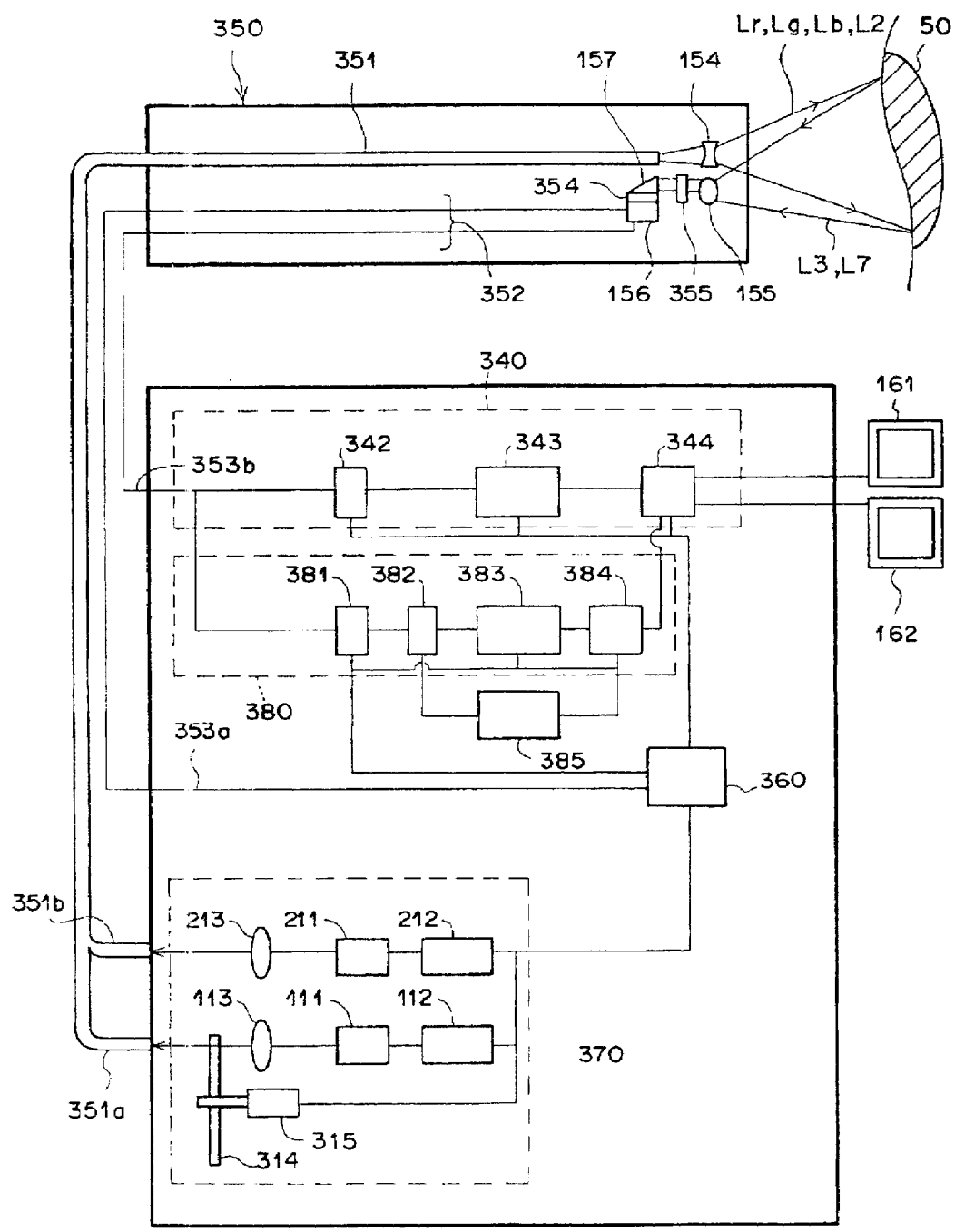
F I G . 13

F I G. 16
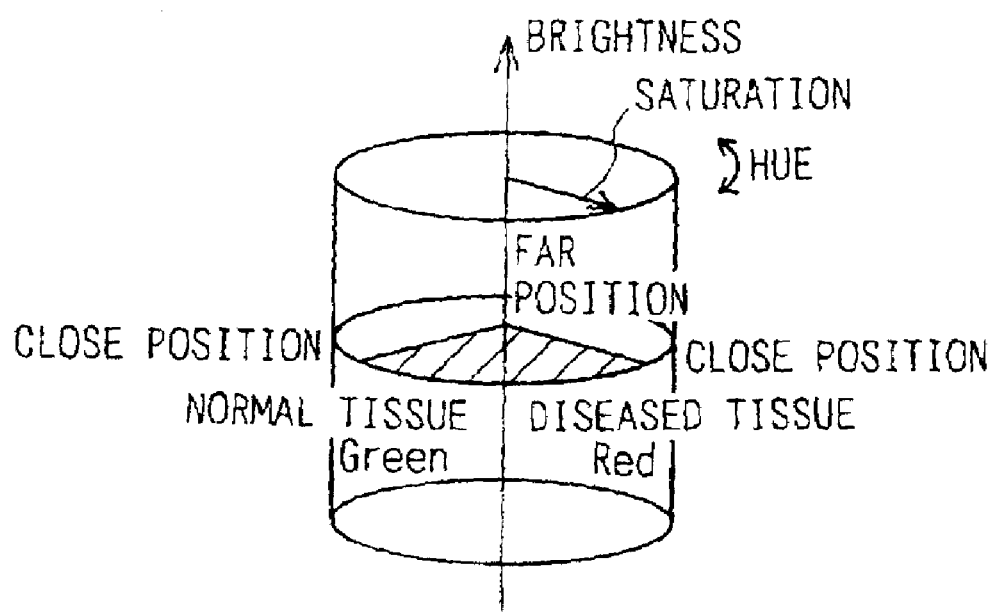

F I G. 20A
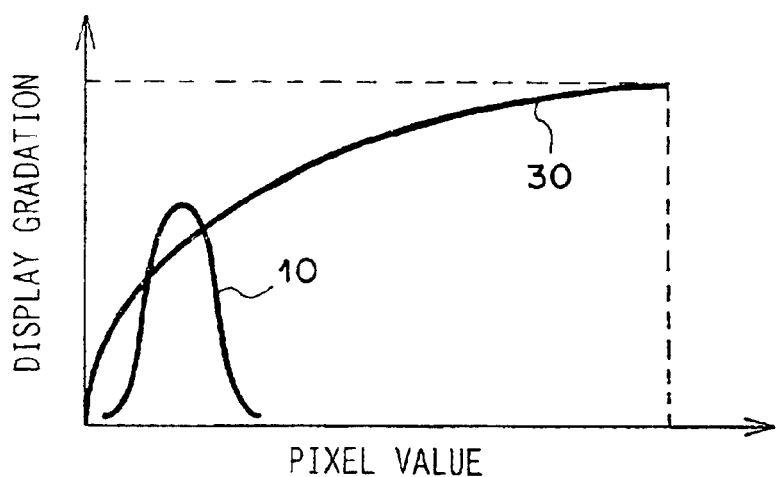
F I G. 20B 
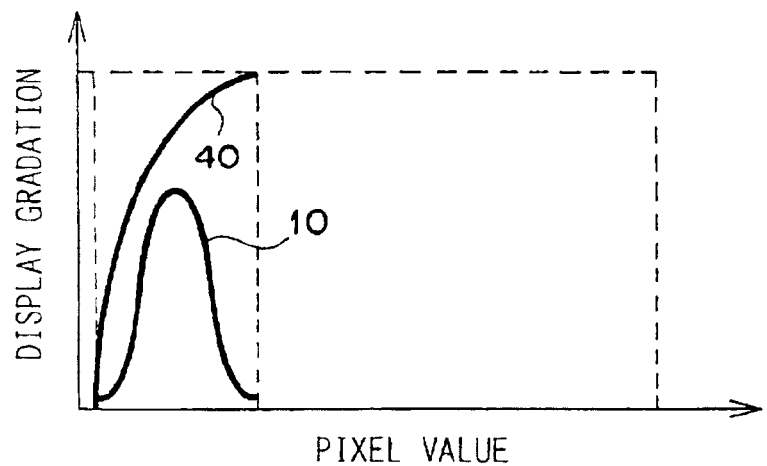

FLUORESCENT-LIGHT IMAGE DISPLAY METHOD AND APPARATUS THEREFOR

BACKGROUND OF THE INVENTION

1. Field of the Invention

The present invention relates generally to a fluorescent-light image display method and apparatus therefor, and more particularly to a method of and apparatus for detecting the fluorescent-light emitted from a living-tissue subject upon irradiation thereof by a stimulating-light and displaying the detected fluorescent light as an image representing the data relating to the living-tissue subject.

2. Description of the Related Art

It has been known in the field of radiology that when a living-tissue subject is irradiated by a stimulating wavelength having a predetermined wavelength, the strength of the fluorescent light emitted from the normal tissue and the strength of the fluorescent light emitted from the diseased tissue differ. Technologies have been proposed, wherein, by making use of this difference, a living-tissue subject is irradiated by a stimulating-light of a predetermined wavelength and by receiving the fluorescent-light image emitted from the living-tissue subject, the location and range of infiltration of a diseased tissue is displayed as a fluorescent-light image.

Normally, upon irradiation by stimulating-light, as shown in FIG. 21, because a strong fluorescent-light is emitted from normal tissue and a weak fluorescent-light is emitted from diseased tissue, by measuring the strength of the fluorescent light, the state of the disease can be determined.

Basically, this type of fluorescent-light image display apparatus comprises a stimulating-light emitting means for projecting the stimulating-light onto a living-tissue subject, a fluorescent-light image obtaining means for obtaining a fluorescent-light image of the fluorescent light emitted from the living-tissue subject, and a display means for receiving the output of the fluorescent-light image obtaining means and displaying aforementioned fluorescent-light image. In many cases, this apparatus is incorporated into an endoscope for insertion into a body cavity of a patient, a colposcope, or a surgical-use microscope.

However, when using a fluorescent-light image display apparatuses such as that described above, because there is unevenness on a the surface of a portion of the living-tissue subject, the distance between the stimulating-light emitting system and the living-tissue subject is not uniform, and the intensity of the stimulating-light irradiating a living-tissue subject is generally not uniform at all positions of the living-tissue subject. The strength of the fluorescent light emitted from the living-tissue subject is substantially proportionate to the degree of the stimulating-light irradiation received by the living-tissue subject, and the degree of stimulating-light irradiation received by the living-tissue subject is in inverse proportion to the square of the distance. Therefore, there are cases in which a diseased tissue located closer to the stimulating-light emitting system emits a stronger fluorescent light than a normal tissue located at a position further removed from the stimulating-light emitting system, and if an operator makes a determination as to the state of the disease based solely on the strength of the fluorescent light, an erroneous diagnosis result is obtained.

In order to reduce the uncertainty and itinerant precariousness in diagnosis due to the circumstances described above, the applicants of the present application propose a fluorescent-light image display apparatus for displaying a pseudo color image, wherein a narrow-band fluorescent-light image near the 480 nm wavelength range is obtained of the normal tissue, and a wide-band fluorescent-light image of the fluorescent light in the visible spectrum is obtained of the diseased tissue, a division value is obtained of the light strength of the wide-band image fluorescent-light image, and based on this division value, aforementioned pseudo color image is displayed.

That is to say, the term representing the strength of the fluorescent light, which is dependent on the distance between the stimulating-light source and the living-tissue subject, is cancelled by aforementioned division process, and an image displaying only the difference in the spectra of the fluorescent light is obtained.

Further, on the other hand, the applicants of the present application propose a method of facilitating discernment of the state of a living-tissue subject by obtaining the ratio of the strength of the stimulating-light received by the irradiated living-tissue subject and the fluorescent light emitted therefrom, that is, the value reflecting the fluorescent light emission output, which is a value that is not affected by the distance or angle from which the stimulating-light has been projected onto the living-tissue subject.

When obtaining the value reflecting aforementioned fluorescent light emission output, because the stimulating-light is not absorbed the same by the various types of tissue, even if the distribution of the light strength of the irradiated stimulating-light is measured, the distribution of the light strength of the stimulating-light received by the living-tissue subject is not correctly measured.

Here, one strategy for obtaining the fluorescent light uptake rate is to irradiate a living-tissue subject with a near-infrared light, which is absorbed uniformly by various types of tissue, as a reference light and to photograph a reflected-light image of the reflected reference-light reflected from the living-tissue subject; the light strength of this reflected-light image is used in place of the light strength of the stimulating-light received by the living-tissue subject and a division value of the fluorescent-light image and the light strength of the reflected-light image is obtained, and based on this division value, a pseudo color image is displayed.

That is to say, by aforementioned division process, the term representing the light strength of the fluorescent-light, which is dependent on the distance between the stimulating-light source and the living-tissue subject is cancelled, and an image reflecting only the difference in the fluorescent light emission output is obtained.

However, as described above, by performing aforementioned division process between fluorescent-light images or between a fluorescent-light image and a reflected-light image, although the pseudo color image in which the distance data has been cancelled contains the data relating to the fluorescent light emitted from the living-tissue subject, after being used as a diagnostic tool for determining the state of a disease, it becomes a composite-image in which the valuable data relating to the form of the living-tissue subject has been omitted. And once again, to the operator, the composite-image gives the impression of flatness devoid of any unevenness whatsoever, and becomes considered as a dubious image.

SUMMARY OF THE INVENTION

The present invention has been developed in consideration of the circumstances described above, and it is a primary objective of the present invention to provide a fluorescent-light image display method of and apparatus for displaying an image containing the data of the fluorescent light emitted from a living-tissue subject and the data relating to the form of the living-tissue subject, and which does not make the operator doubt the accurateness with which a diagnosis can be made based on the use of said image.

In addition, in order to display, as described above, an image that contains the information relating to the form of the living-tissue subject under examination, for cases in which a brightness image is formed based on the light strength of the reflected-light image, and a diagnostic image is obtained by combining this brightness image with aforementioned pseudo color image, when the strength of the reflected-light due to the reference light that has been illuminated is weak, because the brightness image based on the strength of the reflected-light is a monochrome image, the overall image becomes dark, and there are cases in which it is not possible to visually recognize the living-tissue subject under examination. For example, for cases in which the fluorescent-light image display apparatus described above is provided as an integral part of an endoscope for insertion into a body cavity of a patient, a colposcope, a surgical-use microscope, etc., when the insertion portion has been inserted into the environs of the living-tissue subject under examination, because the forward end thereof is not fixedly attached the distance between the forward end of the insertion portion and the living-tissue subject under examination reaches the range of several millimeters to 50 mm. Accordingly, when the distance between the forward end of the insertion portion and the living-tissue subject under examination is toward the upper end of this range, the strength of the reflected-light due to the reference light that has been illuminated becomes weak, and as a result, the brightness image becomes dark overall and the living-tissue subject under examination is unable to be recognized visually.

In view of this, it is a further object of the present invention to provide a fluorescent-light image display apparatus capable of displaying a diagnostic image having adequate brightness even when the strength of the reflected-light due to the reference light that has been illuminated becomes weak.

The first fluorescent-light image display method according to the present invention comprises obtaining a fluorescent-light image based on the strength of the fluorescent light emitted from a target area upon irradiation thereof by a stimulating-light, assigning at least one of color data and brightness data to a computed-image based on the fluorescent-light image and forming a tissue-state image representing mainly the state of the living-tissue subject of the target area, assigning at least one of the color data and brightness data corresponding to the color data and brightness data assigned to the tissue-state image to the fluorescent-light image and forming a tissue-state image representing mainly the form of the living-tissue subject of the target area, combining the tissue-state image and the tissue-form image to form a composite-image, and displaying the composite-image.

Here, the expression "a computed-image based on the fluorescent-light image" can refer to for example, an image computed based on the ratio of one to another of two wavelength components among a plurality of wavelength components of said fluorescent-light image, each of said wavelength components representing a different wavelength band of fluorescent light. Note that the referents of the expression "division value" include values such as the value computed by adding a correction value to the pixel values of a fluorescent-light image and then performing division, the value obtained by subjecting the value obtained by division to arithmetical processing, values categorized by division, and etc. Further, the fluorescent-light image itself can be used as a computed-image.

In addition, the expression "color data" refers to, for example, the hue, saturation, chromaticity (hue and saturation) occurring in a color appearance system (an HSB/HVC/LAB/Luv/La*b*/Lu*v* color space) okra color mixing system (an XYZ color space), or the color difference (such as the IQ of the YIQ, the CbCr of the YcbCr, etc. of an NTSC signal) etc.

Further, the expression "brightness data" refers to, for example, the brightness or luminosity occurring in a color appearance system (an HSB/HVC/LAB/Luv/La*b*/Lu*v* color space) or a color mixing system (an XYZ color space), or the brightness (such as the Y of the YIQ, the Y of the YcbCr, etc. of an NTSC signal) etc.

Still further, the expression "assigning at least one of color data and brightness data to a computed-image" refers to assigning to each pixel of a computed-image a numerical value representing at least one of a different hue, saturation, chromaticity, brightness, and etc., corresponding to the size of the pixel values thereof.

Further still, the expression "assigning at least one of color data and brightness data corresponding to the color data and brightness data assigned to the tissue-state image to the fluorescent-light image" refers to, assigning at least one of an appropriate hue, saturation, chromaticity, brightness, and etc. to the fluorescent-light image, based on consideration of the combination of color data and brightness data assigned to the computed-image, as described above.

The second fluorescent-light image display method according to the present invention comprises obtaining a fluorescent-light image based on the strength of the fluorescent light emitted from a target area upon irradiation thereof by a stimulating-light, obtaining a reflected-light image based on the strength of the reflected-light reflected from a target area upon irradiation thereof by a reference light, assigning at least one of color data and brightness data to a computed-image based on the fluorescent-light image and forming a tissue-state image representing mainly the state of the living-tissue subject of the target area, assigning at least one of the color data and brightness data corresponding to the color data and brightness data assigned to the tissue-state image to the reflected-light image and forming a tissue-state image representing mainly the form of the living-tissue subject of the target area, combining the tissue-state image and the tissue-form image to form a composite-image, and displaying the composite-image.

Here, the expression "a computed-image based on the fluorescent-light image" can refer to for example, an image computed based on the ratio of one to another of two wavelength components among a plurality of wavelength components of the initially obtained fluorescent-light image, each of said wavelength components representing a different wavelength band of fluorescent light, or based on the ratio of a fluorescent-light image of a predetermined wavelength band to the reflected-light image; and a division value can be used as aforementioned ratio. Note that the referents of the expression "division value" include values such as the value computed by adding a correction value to the pixel values of a fluorescent-light image and then performing division, the value obtained by subjecting the value obtained by division to arithmetical processing, values categorized by division, and etc. Further, the fluorescent-light image itself can be used as a computed-image.

Additionally, the expression "assigning at least one of the color data and brightness data corresponding to the color data and brightness data assigned to the tissue-state image to the reflected-light image" refers to, assigning at least one of an appropriate hue, saturation, chromaticity, brightness, and etc. to the reflected-light image, based on consideration of the combination of color data and brightness data assigned to the computed-image, as described above.

Further, according to the first and second fluorescent-light image display methods described above, a statistical quantity of the pixel values of any one of the obtained images can be computed, and a display gradation of the brightness data assigned to the obtained image of which the statistical quantity has been obtained, based on said statistical quantity.

Here, the expression "any one of the obtained images" refers to: in the first fluorescent-light image display method, to aforementioned computed-image or aforementioned fluorescent-light image; and in the second fluorescent-light image display method, to aforementioned computed-image, aforementioned fluorescent-light image, or aforementioned reflected-light image.

Still further, the expression "statistical quantity" refers to, for example, the average value of the pixel values, the standard deviation value of the pixel values, the highest and the lowest pixel value, etc., however, as far as it represents a statistical quantity, any of a number of such type of values will suffice.

In addition, the expression "a display gradation of the brightness data is assigned, based on said statistical quantity refers to the assigning, based on the statistical quantity or on a combination of a plurality of the statistical values (such as: the average value and the standard deviation value; the average value and the largest value; the average value and the largest value and the smallest value; the average value and the standard deviation value and the largest value and the smallest value; the largest value and the standard deviation value; the largest value and the smallest value; the largest value and the smallest value and the standard deviation value, and etc.) to each pixel value of the obtained image of which the statistical quantity has been computed a numerical value representing a display gradation of the brightness data, corresponding to the size of each of said pixel values.

Further, the statistical quantity can be computed of a desired portion of any one of the obtained images.

Here, the expression "a desired portion" refers to a section of particular interest and which is desired to be viewed carefully, of any one of the obtained images.

Also, a predetermined coefficient can be computed based on the statistical quantity and any obtained image can be multiplied by the computed coefficient, and a display gradation of the brightness data of any one of the obtained images that has been multiplied by the computed coefficient.

Here, the expression "a predetermined coefficient can be computed based on the statistical quantity" refers to the obtaining of a coefficient according to, for example, the formula (1).

The average value M, and the standard deviation a of the pixel values of any one of the obtained images are designated by desired constants a, b, and c:

$$\text{Upper limit of the display gradation of the brightness data} \times a \approx (M+b\times\sigma)\times c \quad (1)$$

Accordingly, the expression "a display gradation of the brightness data of any one of the obtained images that has been multiplied by the computed coefficient" refers to, as shown in FIG. 19, by multiplying a pixel value distribution 10 by the coefficient, a pixel value distribution 20 is obtained, and according to a gradation processing function 30 representing a display gradation of the brightness data, a numerical value representing a brightness data is assigned to the value of this pixel value distribution 20.

Further, a gradation processing function representing the display gradation of the brightness data can be determined based on the statistical quantity, and based on the determined gradation processing function, a brightness data can be assigned to any one of the obtained images.

Here, the expression "a gradation processing function representing the display gradation of the brightness data can be determined based on the statistical quantity" refers to, for example, when the pixel value distribution 10 of any one of the obtained images is as the distribution shown in FIG. 20 for the gradation processing function 30, the converting of the gradation processing function 30 to a gradation function 40. That is, the gradation processing function is rewritten so that the:

$$\text{Upper limit of the display gradation of the brightness data} \times a \approx M+b\times\sigma$$

$$\text{Lower limit of the display gradation of the brightness data} \times a \approx M-b\times\sigma$$

More specifically, when the pre-conversion gradation processing function is such that: f (x), MIN=M−b×σ, and Max=M+b×σ, the gradation processing function is rewritten so that f (x−Min/(Max−Min))

Accordingly, the expression "based on the determined gradation processing function, a brightness data can be assigned to any one of the obtained images", refers to the assigning of a numerical value representing a display gradation of the brightness data, according to the gradation processing function 40, to the pixel value distribution 10.

The first fluorescent-light image display apparatus according to the present invention comprises a fluorescent-light image obtaining means for obtaining a fluorescent-light image based on the strength of fluorescent light emitted from a target area upon irradiation thereof by a stimulating-light, a tissue-state image forming means for assigning at least one of color data and brightness data to a computed-image based on said fluorescent-light image and forming a tissue-state image representing mainly a state of tissue in the target area, a tissue-form image forming means for assigning to said fluorescent-light image at least one of color data and brightness data corresponding to the color data and the brightness data assigned to said tissue-state image and forming a tissue-form image representing mainly a form of the tissue in the target area, a composite-image forming means for combining the tissue-state image and the tissue-form image to form a composite-image, and a display means for displaying the composite-image formed by said composite-image forming means.

The second fluorescent-light image display apparatus according to the present invention comprises a fluorescent-light image obtaining means for obtaining a fluorescent-light image based on strength of the fluorescent light emitted from a target area upon irradiation thereof by a stimulating-light, a reflected-light image obtaining means for obtaining a reflected-light image based on strength of the reflected-light reflected from the target area upon irradiation thereof by a reference light, a tissue-state forming means for assigning at least one of color data and brightness data to a computed-image based on said fluorescent-light image and forming a tissue-state image representing mainly a state of tissue in the target area, a tissue-form image forming means for assigning to said reflected-light image at least one of color data and brightness data corresponding to the color data and the brightness data assigned to said tissue-state image and forming a tissue-form image representing mainly a form of the tissue in the target area, a composite-image forming means for combining the tissue-state image and the tissue-form image to form a composite-image, a display means for displaying the composite-image formed by said composite-image forming means.

In addition, according to the first and second fluorescent-light image display apparatuses of the present invention, the computed-image can be an image based on the ratio of one to another of two wavelength components among a plurality of wavelength components of a fluorescent-light image each of said wavelength bands being a different wavelength band of fluorescent light.

Further, according to the second fluorescent-light image display apparatus of the present invention, the computed-image can be an image based on the ratio between a fluorescent-light image and a reflected-light image.

Still further, the first and second fluorescent-light image display apparatuses according to the present invention can be provided with a statistical-quantity computing means for computing a statistical quantity of the pixel values of any one of the obtained images, and a gradation processing means for assigning, to any one of the obtained images of which a statistical quantity has been computed, a display gradation based on the statistical quantity.

Further still, the statistical-quantity computing means can be a means for computing the statistical quantity from a desired portion of any one of the obtained images.

Still further, the gradation processing means can be a means for computing a predetermined coefficient based on the statistical quantity, multiplying any one of the obtained images of which the statistical quantity has been obtained by said computed coefficient, and assigning a display gradation of the brightness data to any one of the obtained images that has been multiplied by the coefficient.

Additionally, the gradation processing means can be a means for determining a gradation processing function representing the display gradation of the brightness data based on the statistical quantity, and assigning the display gradation of the brightness data, based on said determined gradation processing function, to any one of the obtained images.

In addition, the first and second fluorescent-light image display apparatuses according to the present invention can be provided with a bit-shifting means for bit-shifting the pixel values of said one of the obtained images when each of said pixel values is represented by data of 9 bits or more, so that each of said pixel values is represented by the data of the first 8 bits or less, wherein the statistical-quantity computing means computes the statistical quantity based on said bit-shifted data.

Here, the expression "so that each of said pixel values is represented by data of 8 bits or less" refers to the rounding off of the bits following the first 8-bits of data representing a pixel value, so that the computing of a statistical quantity can be performed by a general-use statistical calculator.

Further, the gradation processing means can be a means capable of being turned ON/OFF.

Here, turning "ON" the gradation processing means refers to performing gradation processing, turning "OFF" the gradation processing means refers to not performing gradation processing, and the expression "capable of being turned ON/OFF" refers to the capability of switching between the performing of gradation processing and the non-performing of gradation processing. The expression, "the non-performing of gradation processing" refers to, for example, if gradation processing is performed when brightness data has been assigned to the tissue-state image, regardless of whether the tissue-state is normal or diseased, the luminosity of the image will change, and it becomes impossible to judge the tissue state represented therein. Further, at this point, if a composite-image based on the tissue-state image is displayed without having been subjected to gradation processing, and after once having judged the state of the tissue under examination, the gradation processing is switched to ON and the tissue-state image is subjected to gradation processing, the detailed changes appearing on the examination monitor screen can be viewed.

In addition, even for cases in which brightness data has not been assigned, as it was in the case described above, for example, when the distance between the stimulating-light emitting source becomes suddenly close or far from the target area it is desirable that the gradation processing means is capable of being switched OFF so as to avoid a large change to the display gradation of the brightness data of the image to be displayed.

Further, when the composite-image forming means combines a tissue-state image and a tissue-form image to form a composite-image, when the number of pixels of both images differs, after converting the number of pixels of each of the two images to the number of pixels of either of the two images, the composite-image is formed.

Here, the expression "when the number of pixels of both images differs, after converting the number of pixels of each of the two images to the number of pixels of either of the two images" refers to performing expansion processing, for example, when the number of pixels of one of the two images is 100×100 pixels and the number of pixels of the other is 500×500, by converting each pixel of the image having a number of pixels of 100×100 to a 5×5 unit of pixels, expanding the number of pixels of the 100×100 pixel image to a 500×500 pixel image matching the number of pixels of the counterpart image thereto. On the other hand, for cases in which the number of pixels is to be the number of pixels of an image having fewer pixels, reduction processing can be performed; general image processing procedures can be used for aforementioned expansion processing and reduction processing.

Further, the fluorescent-light image display apparatus according to the present invention can be provided in the form of an endoscope apparatus having an endoscope insertion portion to be inserted into the body of a patient.

Still further, a GaN type semiconductor laser can be used as the stimulating-light source, and the wavelength band of the stimulating-light made to be in the 400-420 nm range.

Further still, the first and second fluorescent-light image display apparatuses according to the present invention can be combined with a means for obtaining and displaying a normal-image based on the reflected-light reflected from a target area upon irradiation thereof by a white-light reference light.

In general, the concept "color" is divided into "color as conceived by the color intellect" and "color as perceived by the color visual sense". The expression "color as conceived by the color intellect", also called "sensory color" refers to the colors perceived by the human perceptual faculties, and which are qualitatively defined by use of symbols, color representation, etc. On the other hand, the expression "color as perceived by the color visual sense", also called "color as a psychological physical quantity" is the standardized correlation between quantitatively defined physical quantities of a spectrum of light and the colors perceived as a psychological quantity and measurable in psychological testing. Further, the color appearance system and the color mixing system are color specification systems for displaying color.

The Munsell color system is a color specification system representative of a color appearance system. According to the Munsell color system, colors are defined by three properties: hue, (H); saturation (S); and brightness (V). Hue is divided into the three different colors of red (R), blue(B), and green (G). First, there are five colors that are the base hues: R; yellow (Y); G; B; and purple (P); and these are distributed as five sectors of equal size around the circumference of a single hue ring such as that shown in FIG. 1. Next, the intermediate hues YR, GY, BG, PB, and RP of the base hues are distributed. In general, a reference number 5 is assigned to the base and intermediate hues, and although there are many cases in which there are 100 hues divided into groups of 10 used between adjacent hues, if a rotation angle from 5R, which is a base hue, is used, hues can be represented as continuous values. In this case, for example, 5R can be displayed as H=0 rad, 5Y as H=⅓ rad and 5G as H=⅔ rad.

The luminosity Value V is a standard unit of measure defining the brightness of a color: an ideal black having a 100% reflectance is represented by a luminosity Value of 0; and an ideal white having a reflectance of 100% is represented by a luminosity Value of 10. In general, the human sensory perception of brightness is not proportionate to the reflectance; for example, to recognize a reflectance of 20% as an intermediate brightness, the Munsell brightness standard is substantially proportional to the square root of the reflectance.

The saturation (S) is a standard unit of measure defining the vividness of a color: the vividness is expressed for each brightness and hue by numerical values within a scale starting with gray, which has no vividness and is represented by a value of 0, to the monochrome colors, which are the most vivid.

A saturation is created for each brightness of the hue represented at a distance from the center thereof, and if stacked concentrically in a circular form in order proceeding from the low level brightness's, the 3 properties occurring in the Munsell color system can be expressed as a tube-formed color body, as shown in FIG. 2. All of the colors can be positioned at some point in this color body. In general, sensory color is displayed as three-dimensional coordinate space having a one-dimensional brightness coordinate (called a brightness index), and a two-dimensional coordinate called a conceptual color degree representing an integrated hue and saturation.

On the other hand, the CIE (Commission International de l'Eclairage) color system, which quantitatively treats each color as a mixture of three source stimuli (that is, the light of three source colors) and which has as two main color specification systems the RGB and the XYZ color specification systems, is a color specification system representative of a color mixing system. In practice, it is known that any color can be created by mixing appropriate proportions of the three different independent colors that are the three source stimuli. The three most general source stimuli are R (red), B (blue), and G (green); these three source stimuli, and the three source stimuli values that represent the mixing proportions of the three source stimuli comprise the RGB color specification system. However, in the RGB color specification system, because the plotted equivalent color function may be a negative value according to the wavelength when the three source stimuli values formed by additively mixing continuous spectra of light, difficulty is encountered in function processing. Therefore, coordinate conversion processing is performed so that all of the equivalent color functions are advantageously converted into positive values, and a new color specification system, which defines three imaginary source stimuli X, Y, and Z (i.e., the XYZ color specification system) has been developed in relation to the RGB system. According to the XYZ color specification system, in order to facilitate mathematical treatment, because the equivalent color function of Z (called the brightness) is defined so that it is the equivalent of a relative luminosity factor representing a sensitivity to the human eye with respect to the wavelength. Further, the difference in a color (chromaticity) is defined by the chromaticity coordinate x,y obtained according to the following formula:

$x=X/(X+Y+Z)$ $y=Y/(X+Y+Z)$

FIG. 3 shows a chromaticity chart of the XYZ color specification system. A mixed color of two colors is represented by a point on the straight line connecting two chromaticity points representing the two colors. All the colors appear as points contained with in the region defined by a bell-formd curve (a spectra locus) and the straight line (a pure purple locus) connecting both ends thereof. Further, the arrow mark in center of FIG. 3 indicates the change in hue.

Also, for cases in which color is to be displayed by a TV signal or other representative visual image signal system, the R,G,B components are not transferred as independent colors. For example, according to the NTSC system, the R,G,B components are converted, by use of a predetermined computation, to two color difference signals I,Q and one brightness signal Y. Further, it is also possible to use other systems representative of visible image signal systems, such as the PAL system, etc.

According to the first method of and apparatus for displaying a fluorescent-light image according to the present invention, because: a fluorescent-light image based on strength of fluorescent-light emitted from a target area upon irradiation thereof by a stimulating-light is obtained; at least one of color data and brightness data are assigned to a computed-image based on said fluorescent-light image and a tissue-state image representing mainly a state of tissue in the target area is formed; at least one of color data and brightness data corresponding to the color data and the brightness data assigned to said tissue-state image are assigned to said fluorescent-light image and a tissue-form image representing mainly a form of the tissue in the target area is formed; the tissue-state image and the tissue-form image are combined to form a composite-image; and the composite-image is displayed; the data relating to the fluorescent-light emitted from the target area (data relating to the tissue-state), and the data relating to the tissue-form of the target area can be displayed in 1 composite-image, and moreover, no uncertainty regarding the reliability of the image for use in diagnosis is imparted to the operator.

According to the second method of and apparatus for displaying a fluorescent-light image according to the present invention, because: a fluorescent-light image based on strength of fluorescent-light emitted from a target area upon irradiation thereof by a stimulating-light is obtained; a reflected-light image based on strength of reflected-light reflected from the target area upon irradiation thereof by a reference light is obtained; at least one of color data and brightness data are assigned to a computed-image based on said fluorescent-light image and a tissue-state image representing mainly a state of tissue in the target area is formed; at least one of color data and brightness data corresponding to the color data and the brightness data assigned to said tissue-state image is assigned to said reflected-light image and a tissue-form image representing mainly a form of the tissue in the target area is formed; the tissue-state image and the tissue-form image are combined to form a composite-image; and the composite-image is displayed; the same effect obtained by the first fluorescent-light imaged is play method and apparatus therefor is obtained, and by the forming of the tissue-state image from the reflected-light image based on the illumination of the target area by the reference-light, a composite-image more accurately reflecting the tissue-form of the target area can be displayed.

In addition, according to the first and second methods of and apparatuses for displaying a fluorescent-light image according to the present invention, for cases in which the computed-image is based on ratio between a plurality of wavelength bands of a fluorescent-light image, each of said wavelength bands being a different wavelength band of fluorescent light, because a computed-image reflecting the difference between the form of the fluorescent spectra of the fluorescent light emitted from a target area can be obtained, a composite-image accurately reflecting the tissue-state of the target area can be displayed.

Further, according to the second method of and apparatus for displaying a fluorescent-light image according to the present invention, for cases in which the computed-image is based on the ratio between a fluorescent-light image and a reflected-light image, because a computed-image reflecting the emission output of the fluorescent-light emitted from the target area can be obtained, a composite-image accurately reflecting the tissue-state of the target area can be displayed.

Still further, according to the first and second methods of and apparatuses for displaying a fluorescent-light image according to the present invention, because a statistical quantity is computed of the pixel values of any one of the obtained images, and a display gradation of the brightness data, based on the statistical quantity, is assigned to said any one of the obtained images, even if the pixel values of an image to which brightness data has been assigned are small, a composite-image already having a brightness above a predetermined value can be formed, and also, because the dynamic range of the display gradation of the brightness data can be virtually expanded, a composite-image already capable of visual recognition can be provided. Further, for cases in which an endoscope, etc., that is to be inserted into the body of a patient is used, even when stimulating-light emitting end of the endoscope insertion portion is located a far distance from the target area, because a composite-image already having a brightness above a predetermined value can be formed, composite-images facilitating visual recognition across a wide measurement-distance range can be provided.

Additionally, for cases in which the statistical quantity has been computed of a desired portion of any one of the obtained images, the display gradation of the brightness data can be optimized, an also, the amount of computing required to compute the statistical quantity can be reduced.

In addition, a predetermined coefficient can be computed based on the statistical quantity and aforementioned any one of the obtained images can be multiplied by the computed coefficient, and for cases in which a display gradation of the brightness data is to be assigned to an image that has been multiplied by the computed coefficient, an appropriate display gradation of the brightness data can be assigned by a simpler computation method.

Further, a gradation processing function representing the display gradation of the brightness data can be determined based on the statistical quantity, and for cases in which, based on the determined gradation processing function, a brightness data is to be assigned to any one of the obtained images, the display gradation of the brightness data occurring in a composite-image can be virtually expanded (an equalization effect) by a simpler computation method.

Still further, for cases in which the chromaticity occurring in a color appearance system, the chromaticity occurring in a color mixing system, or the color difference occurring in a visual-image signal system is used as the color data, the color data can be easily assigned to a tissue-state or a tissue-form image.

Further still, for cases in which the luminosity data occurring in a color appearance system, the luminosity occurring in a color mixing system, or the brightness occurring in a visual-image signal system is used as the brightness data, the brightness data can be easily assigned to a tissue-state or a tissue-form image.

In addition, if, for example, the Munsell color system, which is one of color appearance systems, is employed as the color specification system, the color data can be defined corresponding to a hue H occurring in the Munsell color system hue ring shown in FIG. 1, and can easily be made to correspond to only a hue.

Also, if, for example, the XYZ color system, which is a color mixing system, is employed as the color specification system, the color data can be made to correspond to a pair of chromaticity coordinates (x,y) shown in the chromaticity chart in FIG. 3, and can be easily made to correspond to only a chromaticity.

Further, if, for example, the color difference and brightness occurring in a visual-image signal system are employed, a color-difference signal and a brightness signal can be determined from aforementioned computed-image, etc., and said color-difference signal and brightness signal can be input directly into a video signal circuit, etc., and the color (color difference and brightness) of a composite-image can be determined.

Still further, the mathematical processing occurring when a composite-image is to be formed can be simplified.

Further still, for cases in which pixel values of an image of which a statistical quantity is to be computed are represented by data of 9-bits or more, a bit shifting means is provided to shift the first 8 bits of data so that the pixel value is represented by 8 bits data or less. And for cases in which the statistical-quantity computing means computes the statistical quantity based on the bit-shifted pixel values, the computation can be performed by use of a general-use statistical calculator and high-speed computation processing can be attained.

Additionally, for cases in which ON/OFF switching of the gradation processing of assigning a display gradation of the brightness data, based on the statistical quantity, is possible, even, for example, when the brightness data has been assigned to a tissue-state image, by turning the gradation processing OFF, the tissue-state can be judged accurately, and after once judging the tissue-state, if the gradation processing is switched ON so as to subject the tissue-state image to gradation processing, the detailed changes of the tissue-state within the examination display screen can be viewed.

Further, even for cases in which a brightness data has not been assigned, as described above, to a tissue-state image, if, for example, the distance between the target area and the stimulating-light emitting end of the endoscope insertion portion suddenly becomes close, or far, because the gradation processing can be switched OFF, a large fluctuation in the display gradation of the brightness data of an image to be displayed can be avoided.

Further still, for cases in which the statistical quantity is a combination of a plurality of values containing the average pixel value or the largest pixel value, the computation of the statistical quantity can be performed comparatively easily, and a display gradation of an appropriate brightness can be assigned.

In addition, when combining the tissue-state and the tissue-form image to form a composite-image, if the number of pixels of both images is different, after converting the number of pixels of both images to the number of pixels of either of the two images, because a composite-image is to be formed, after, for example, making the number of pixels of the image having fewer pixels match the number of pixels of the image having the larger number of pixels, for cases in which a composite-image is formed based on both images, because, for example, the quantity of fluorescent light is small, when the fluorescent-light image is obtained, it is necessary that the fluorescent-light image be subjected to binning processing, etc., and even for cases in which the number of pixels of the fluorescent-light image is less than the number of pixels of the reflected-light image, the number of pixels of the composite-image can be matched to the number of pixels of the reflected-light image and the composite-image displayed, and the tissue-state of the target area can be accurately displayed.

Further, if, for example, the number of pixels of the image having the larger number of pixels is made to match the number of pixels of the image having fewer pixels, for cases in which a composite-image is to be formed based on both images, the need to perform excessive computation processing is eliminated and the image processing can be carried out at high-speed.

Still further, if a GaN type semiconductor laser is used as the stimulating-light source, a cost-effective small-sized light source can be provided, and also, if the wavelength band of the simulating light is in the 400-420 nm range, fluorescent light is efficiently emitted from a target area irradiated thereby.

BRIEF DESCRIPTION OF THE DRAWINGS

FIG. 1 is a drawing provided for explanation of the hue ring according to the Munsell color specification system, FIG. 13 is a schematic drawing of a fluorescent endoscope apparatus according to the sixth embodiment of the present invention, FIG. 16 shows the color range of a composite-image displayed by a fluorescent endoscope apparatus according to the eighth embodiment of the present invention, FIGS. 20A and 20B are graphs provided for explanation of the operation for changing the gradation processing function and assigning a display gradation of the brightness data.

DESCRIPTION OF THE PREFERRED EMBODIMENTS

Figure 4:
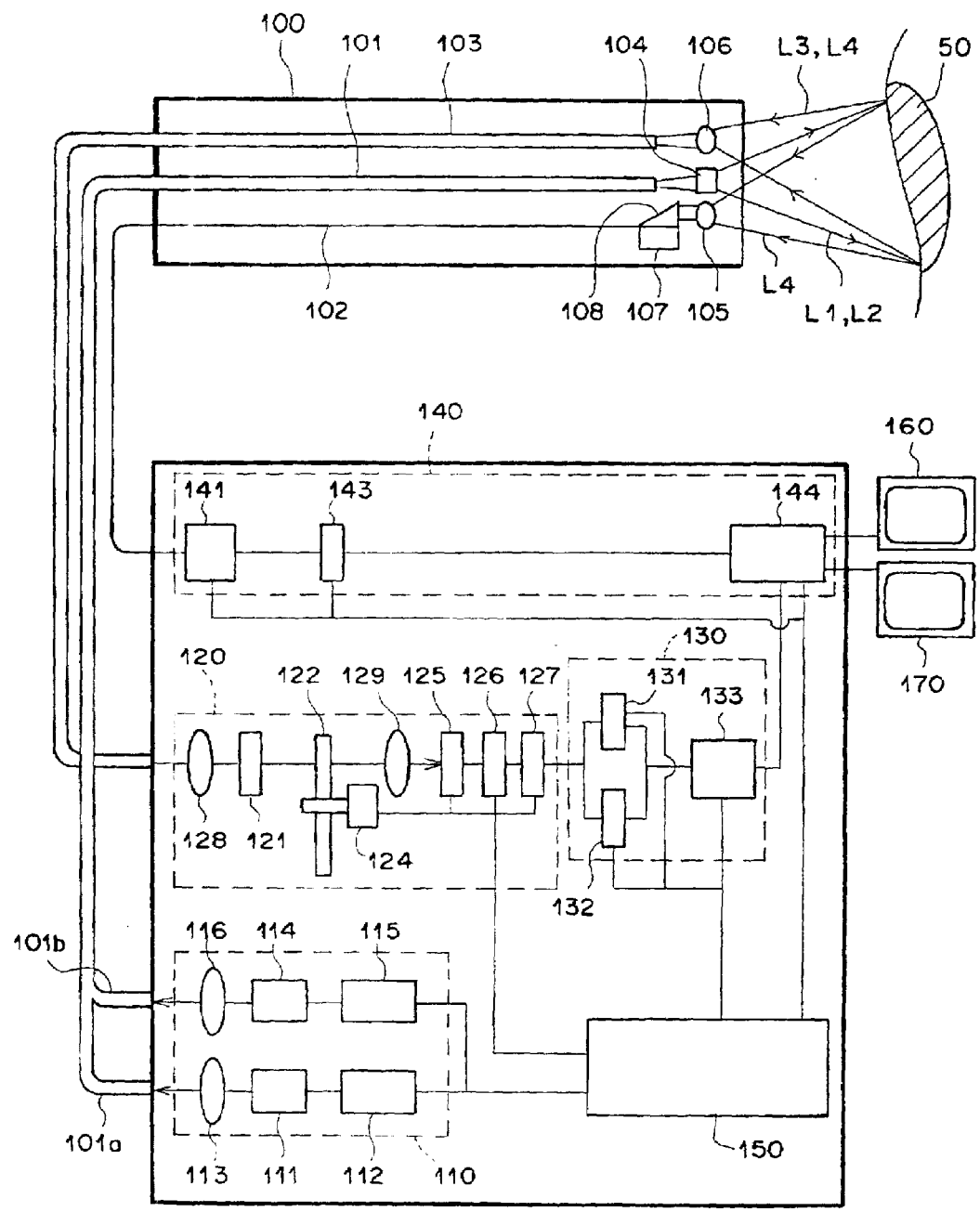
FIG. 4 is a schematic drawing of a fluorescent endoscope apparatus according to the first embodiment of the present invention.

Hereinafter, with reference to the drawings, the preferred embodiments of the present invention will be explained. First, with reference to FIGS. 4 and 5, the first embodiment of a fluorescent endoscope apparatus implementing a fluorescent-light image display apparatus implementing the fluorescent-light image display method according to the present invention will be explained. FIG. 4 is a schematic drawing of a fluorescent endoscope apparatus implementing a fluorescent-light image display apparatus according to the present invention. According to the fluorescent-light image display apparatus of the current embodiment: the fluorescent light emitted from a living-tissue subject is two-dimensionally detected by an image fiber; a narrow-band fluorescent-light image having a wavelength band of 430-530 nm and a wide-band fluorescent-light image having a wavelength band of 430 -730 nm are obtained; a computed-image based on the division value between the pixel values of both images is formed; a hue signal H determining a hue H occurring in the Munsell color system is assigned to said computed-image and a tissue-state image representing mainly the tissue-state of the target area is formed; an IR reflected-light image formed of the light reflected from the living-tissue subject under examination upon illumination thereof by white-light is obtained; a luminosity V occurring in the Munsell color system is assigned to said IR reflected-light image and a tissue-state image reflecting mainly the tissue-form of the target area is formed; and a composite-image combining the tissue-state image and the tissue-form image is displayed on a monitor.

The fluorescent endoscope apparatus according to the first embodiment of the present invention comprises: an endoscope insertion portion 100 to be inserted into the body of the patient to the position at which the primary nidus of a disease and areas of suspected secondary infection are located; an illuminating unit 110 for emitting normal-image and IR reflected-light image obtaining-use white-light and fluorescent-light image obtaining-use stimulating-light; an image obtaining unit 120 for obtaining two fluorescent-light images having different wavelength bands and a reflected-light image; a composite-image forming unit 130 for computing a division value between the fluorescent-light images, assigning a hue to a computed-image based on said division value and forming a tissue-state image, assigning a luminosity V to the pixel values of an IR reflected-light image and forming a tissue-form image, and combining the tissue-state image and the tissue-form image to form a composite-image; an image processing unit 140 for performing the image processing required in order to display the normal-image and the composite-image as visible images; a control computer 150, which is connected to each of the units, for controlling the operation timing thereof, a monitor 160 for displaying as a visible image the normal-image data processed by the image processing unit 140, and a monitor 170 for displaying as a visible image the composite-image processed by the image processing unit 140.

The endoscope insertion portion 100 comprises a light guide 101 extending to the forward end of the internal portion, a CCD cable 102, and an image fiber 103. The forward end portion of the light guide 101 and the CCD cable 102, that is, the forward end portion of the insertion portion, is provided with an illuminating lens 104 and an objective lens 105. The image fiber 103 is a silicon glass fiber, and is provided at the forward end thereof with a focusing lens 106. A CCD photographing element is connected to the forward end of the CCD cable 102, and a prism 108 is attached to said CCD photographing element 107. The light guide 101 is an integrated cable in which a white-light 101a formed of composite glass fiber and a stimulating-light guide 101b formed of silicon glass fiber are bundled, and the white-light guide 101a and the stimulating-light guide 101b are connected to the illuminating unit 110. One end of the CCD cable 102 is connected to the image processing unit 140, and one end of the image fiber 103 is connected to the image obtaining unit 120.

The illuminating unit 110 comprises a white-light source 111 for emitting normal-image and IR reflected-light image obtaining-use white-light L1 and a white-light use power source 112 electrically connected to said white-light source 111, and a GaN type semiconductor laser 114 for emitting fluorescent-light image obtaining-use stimulating-light L2 and a semiconductor-laser use power source 115 electrically connected to said GaN type semiconductor laser 114.

The image obtaining unit 120 comprises a stimulating-light cutoff filter 121 for cutting off light in the wavelength band below 420 nm, which is close to the wavelength band of the stimulating-light, from the fluorescent light L3 passing through the image fiber 103, a switching filter 122 composed of a combination of three types of optical filters, a filter rotating apparatus 124 for rotating said switching filter 122, a CCD photographing element 125 for obtaining a fluorescent-light image or an IR reflected-light image passing through said switching filter 122, an A/D converting circuit 126 for digitizing a fluorescent-light image and an IR reflected-light image obtained by the CCD photographing element 125, and an image memory 127 for storing an image signal that has been digitized by the A/D converting circuit 126.

Figure 5:
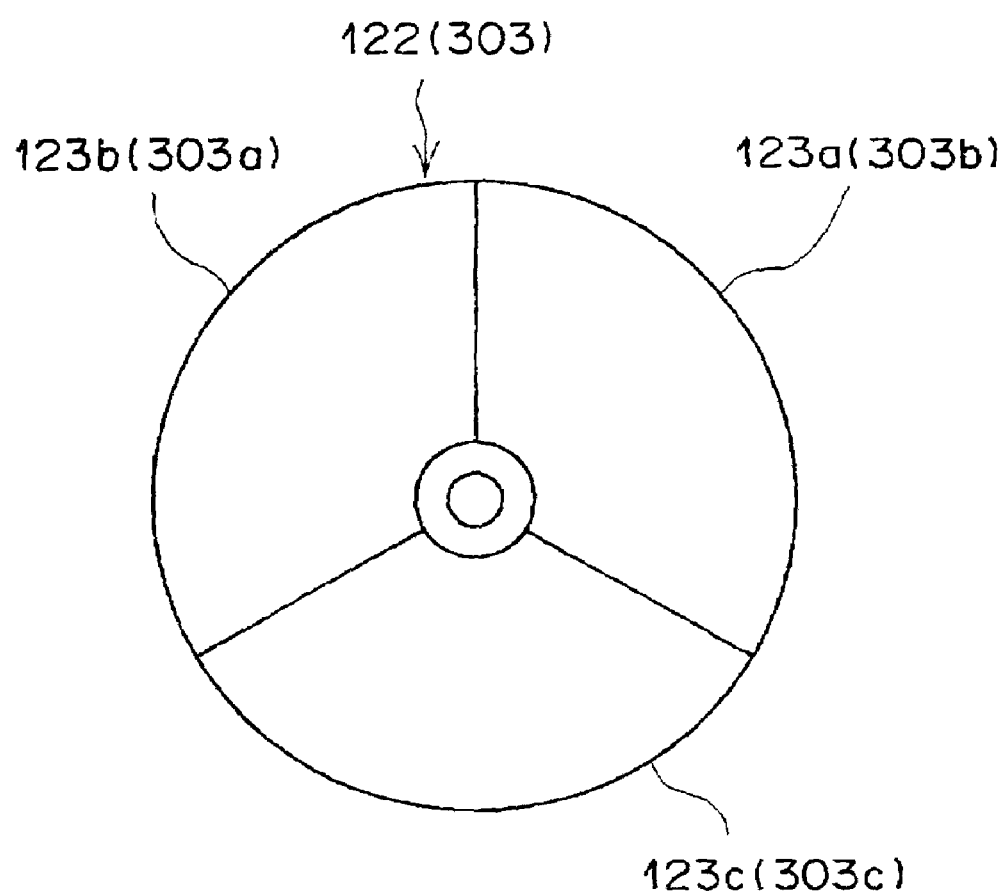
FIG. 5 is a schematic drawing of the switching filter used in the first and second embodiments.

The switching filter 122, as shown in FIG. 5 is formed of an optical filter 123a, which is a band-pass filter for transmitting light in the 430-730 nm wavelength range, an optical filter 123b, which is a band-pass filter for transmitting light in the 480±50 nm wavelength range, and an optical filter 123c, which is a band-pass filter for transmitting light in the 750-900 nm wavelength range. The optical filter 123a is a wide-band fluorescent-light image obtaining-use optical filter; the optical filter 123b is a narrow-band fluorescent-light image obtaining-use optical filter, and the optical filter 123c is an IR reflected-light image fluorescent-light image obtaining-use optical filter. When the switching filter 122 is irradiated with the white-light L1, the optical filter 123c is disposed above the optical path, and when irradiation by the stimulating-light L2, the control computer 150 implements controls so that the optical filter 123a and 123b are alternately disposed above the optical path by the filter rotating apparatus 124.

The CCD photographing element 125 is a 500×500 pixel obtaining element, and when obtaining an IR reflected-light image, under control of the control computer 150, normal readout is carried out, however, when obtaining a fluorescent-light image, because the signal of the fluorescent-light image is raised, binning readout is performed after outputs of 5×5 individual pixels are added. Therefore, when obtaining a fluorescent-light image, the image obtaining element operates as an image obtaining element having 100×100 pixels.

The image memory 127 comprises a narrow-band fluorescent-light image memory zone, a wide-band fluorescent-light image memory zone, and an IR reflected-light image memory zone, which are not shown in the drawings. The narrow-band fluorescent-light image obtained when the living-tissue subject is irradiated by the stimulating-light L2 and in a state in which the narrow-band fluorescent-light image obtaining-use optical filter 123a is disposed above the optical path is stored in the narrow-band fluorescent-light image memory zone, and the wide-band fluorescent-light image obtained when the living-tissue subject is irradiated by the stimulating-light L2 and in a state in which the wide-band fluorescent-light image obtaining-use optical filter 123b is disposed above the optical path is stored in the wide-band fluorescent-light image memory zone. Further, the IR reflected-light image obtained when the living-tissue subject is illuminated with the white-light L1 and in a state in which the IR reflected-light image obtaining-use optical filter 123c is disposed above the optical path is stored in the IR reflected-light image obtaining-use image memory zone.

As described above, because the readout method differs, the number of pixels of the IR reflected-light image is 500×500, and the number of pixels of the narrow-band fluorescent-light image and the wide-band fluorescent-light image is 100×100.

The image composing unit 130 comprises a tissue-state image forming means 131 provided with a prerecorded look-up table correlating the range of division value between the fluorescent-light images and the hue H occurring in the Munsell hue ring (0 rad – $\frac{2}{3}$ rad, Red-Yellow-Green range) for assigning a hue H to the computed image and forming a tissue-state image, a tissue-form image forming means 132 provided with a prerecorded look-up table correlating the pixel value range of an IR reflected-light image and a luminosity V (Value) occurring in the Munsell color system, and an composite-image forming means 133 for forming a composite-image based on the tissue-state image and the tissue-form image.

The image processing unit 140 comprises a signal processing circuit 141 for forming a normal-image, which is a color image, from the signal obtained by the CCD photographing element 107, an A/D converting circuit 142 for digitizing the normal-image obtained by said signal processing circuit 141, a normal-image memory 143 for storing the digitized normal-image, and a video signal processing circuit 144 for converting to a video image signal the normal-image output from said normal-image memory 143 and the composite-image composed by the image composing portion 143.

Hereinafter, the operation of a fluorescent endoscope apparatus of the configuration described above and implementing the fluorescent-light image display apparatus according to the present invention will be described. According to the fluorescent endoscope of the current embodiment, the obtaining of a normal-image and an IR reflected-light image, and the obtaining of a fluorescent-light image are performed alternately in a time division manner. First, the operation occurring when a fluorescent-light image is to be obtained will be explained.

According to the fluorescent endoscope apparatus of the current embodiment, based on a signal from the control computer 150, the semiconductor-laser use power source 115 is activated, and stimulating-light L2 having a wavelength of 410 nm is emitted from the GAN type semiconductor laser 114. The stimulating-light L2 passes through the stimulating-light use focusing lens 116 and enters the stimulating-light guide 101b, and after being guided to the stimulating-light emitting end of the endoscope insertion portion, the white-light L1 is projected onto the living-tissue subject 50 by illuminating lens 104.

The fluorescent light L3 emitted from the living-tissue subject 50 upon irradiation thereof by the stimulating-light L2 is focused by lens 106 and enters the forward end of the image fiber 103. After passing through the image fiber 103, the fluorescent light L3 is focused by the lens 128 and passes through the stimulating-light cutoff filter 121, the switching filter 122 and the optical filters 123a and 123b.

The optical filter 123a is a band-pass filter that transmits only light in the 430-730 nm wavelength range, and the fluorescent transmitted by the optical filter 123b becomes a wide-band fluorescent-light image. The optical filter 123b is a band-pass filter that transmits only light in the 480±50 nm wavelength range, and the fluorescent transmitted by the optical filter 123b becomes a narrow-band fluorescent-light image.

The wide-band fluorescent-light image and the narrow-band fluorescent-light image are received by the CCD photographing element 125, and after being electrically converted, 5×5 pixel signal portions are readout using a binning readout process, said wide-band and narrow-band fluorescent-light images are digitized by the A/D converting circuit and stored in the wide-band fluorescent-light image memory zone and the narrow-band fluorescent-light image memory zone, respectively, of the image memory 127. By performing the binning readout process described above, a fluorescent-light image having a weak light strength can be obtained with a high degree of accuracy, however, the number of pixels of the fluorescent-light image becomes 100×100, which is 1/25 the number of when normal readout is performed.

Next, the operation occurring when an IR reflected-light image is to be obtained will be explained. First, the white-light use power source 112 is activated based on a signal from the control computer 150, and the white-light L1 is emitted from the white-light source 111. The white-light L1 passes through the white-light use focusing lens 113 and enters the white-light guide 101a, and after being guided to the stimulating-light emitting end of the endoscope insertion portion, the white-light L1 is projected onto the living-tissue subject 50 by an illuminating lens 104. The reflected-light L4 of the white-light L1 is focused by the focusing lens 106 and enters the forward end of the image fiber 103. After passing through the image fiber 103, the reflected-light L4 is focused by the lens 128 and is transmitted by the stimulating-light cutoff filter 121, the switching filter 122, and the optical filter 123c.

Because the optical filter 123c is a band-pass filter that transmits only light in the 750-900 nm wavelength range, the IR reflected-light image transmitted by the optical filter 123c becomes an IR reflected-light image composed only of the near-infrared wavelength light within the reflected-light L4 transmitted by the optical filter 123c.

This IR reflected-light image is received and electrically converted by the CCD photographing element 125, and after being digitized by the A/D converting circuit 126, is stored in the IR reflected-light image memory zone of the image memory 127.

Next, the operation occurring when a composite-image is to be formed will be explained. First, the tissue-state image forming means 131 of the composite-image forming unit 130 divides the pixel value of each of the pixels of the narrow-band fluorescent-light image stored in the narrow-band fluorescent-light image memory zone of the image memory 427 by the corresponding pixel value each of the pixels of the wide-band fluorescent-light image stored in the wide-band fluorescent-light image memory zone of the image memory 427, assigns a hue H (Hue) occurring in the Munsell color system, by use of the division value and the prerecorded look-up table, and forms a tissue-state image, which is output to the image composing portion 133.

In addition, the tissue-form image forming means 132 assigns a luminosity V occurring in the Munsell color system, by use of the pixel value and the prerecorded look-up table, for each pixel of the IR reflected-light image stored in the IR reflected-light image memory zone of the image memory 127, and forms a tissue-state image, which it outputs to the image composing portion 133.

The image composing portion 133 converts the data of 1 pixel of a tissue-state image to the data of a 5×5 pixel portion and expands the number of pixels of a 100×100 pixel tissue-state image to 500×500 pixels, and afterwards, combines said 500×500 pixel tissue-state image and the tissue-state image based on the luminosity V and forms a composite-image. Note that, because hue, brightness and saturation (three attributes of color) are required when the image is to be displayed in color, the saturation occurring in the Munsell color system is set at the highest value of each hue and brightness when composing a composite-image.

After that, RGB conversion is preformed using the formula below, and the composite-image formed is output to the video signal processing circuit 144:

$R = V/3 + 2S \cos(H/6)$ $G = V/3 - S \cos(H/6) + S \sin(H/2)$ $B = V/3 - S \cos(H/6) - S \sin(H/2)$ The composite-image converted to a video signal by the video signal processing circuit 144 is input to the monitor 170 and displayed on said monitor as a visual image. The continuous operation described above are controlled by the control computer 150.

Next, the operation occurring when a normal-image is to be obtained will be explained. When a normal-image is to be obtained, at the same time as the reflected-light image described above, first, the white-light use power source 112 is activated and the white-light L1 is emitted from the white-light source 111. The white-light L1 enters the white-light guide 101a through by way of the white-light use focusing lens 113, and after being guided to the stimulating-light emitting end of the endoscope insertion portion, is projected onto the living-tissue subject 50 by the illuminating lens 104.

The reflected-light L4 of the white-light L1 is focused by the objective lens 105, reflected by the prism 108 and focused by the CCD photographing element 107.

The visible image signal from the CCD photographing element 107 is input to the A/D converting circuit 142, and after being digitized, is stored in the normal-image memory 143. The normal-image stored in the normal-image memory 143, after being converted to a video signal by the video signal processing circuit 144, is input to the monitor 160 and displayed on said monitor 160 as a visible image. The continuous operation described above is controlled by the control computer 150.

According to the operation described above, because the hue of the displayed composite-image reflects the division value of the pixel values between two types of fluorescent-light images, that is, the difference in the form of the fluorescent spectra emitted from the living-tissue subject 50, and because the luminosity reflects the pixel values of the IR reflected-light image, that is, the form of the living-tissue subject 50, the data relating to the fluorescent light emitted from the living-tissue subject 50 as well as the data relating to the form of the living-tissue subject of the target area can be displayed in one image, and no doubt as to the reliability of the composite-image for use in diagnosis is imparted to an operator. Therefore, an operator can easily judge the tissue-state of the target area.

Further, by determining the hue H occurring in the Munsell hue ring, based on the division value between the pixels of the fluorescent-light images, the division value of the pixels values can be made to correspond only to the hue, and the precise difference in the form of the fluorescent spectra of the fluorescent light can be reflected in a composite-image.

In addition, because the fluorescent-light images have been readout using a binning readout process, the number of pixels forming the fluorescent-light image is 100×100 pixels, however, when forming a composite-image, the data of 1 pixel of a tissue-state image is converted into the data of a 5×5 portion of pixels and the 100×100 pixels of the tissue-state image are expanded to 500×500 pixels. Then, because a composite-image has been formed by combining said 500×500 pixel tissue-state image and a tissue state image formed based on the luminosity V, the number of pixels of the display image corresponds to 500×500 pixels, and the form of the target area can be displayed so as to be clearly distinguishable.

Further, because the GaN type semiconductor laser 114 has been used as the light source of the stimulating-light L2, the stimulating-light can be emitted from a small-sized, cost-effective stimulating-light source. In addition, because the wavelength of the stimulating-light is 410 nm, fluorescent light is efficiently emitted from the living-tissue subject 50.

Note that as an example of a different version of the first embodiment described above, when forming a composite-image, instead of determining the hue by using the division value of the pixel values between the fluorescent-light images and the look-up table containing prerecorded hues corresponding to said division value between the fluorescent-light images, another proposed method is to assign a hue using the ratio of the pixel values of two types of fluorescent-light images that have been converted to 16 bit data without reference numerals and a look-up table on which hues are correlated with the 16-bit data, as shown in Table 1. In this case, because the division value between the fluorescent-light images is not used, it is possible to perform a stable mathematical processing even for cases in which the pixel values of the fluorescent light are small, etc.

TABLE 1

| | | Intensity of Narrow-Band Fluorescent-Image | | | |
|---|---|---|---|---|---|
| | | 0 | 1 | 2 | ... 65535 |
| Intensity of Wide-Band Fluorescent-Image | 0 | H = 2/3rad | | | |
| | 1 | ... | H = 2/3rad | | |
| | 2 | ... | ... | H = 2/3rad | |
| | ... | ... | ... | ... | ... |
| | 65535 | H = 0rad | | | H = 2/3rad |

Figure 6:
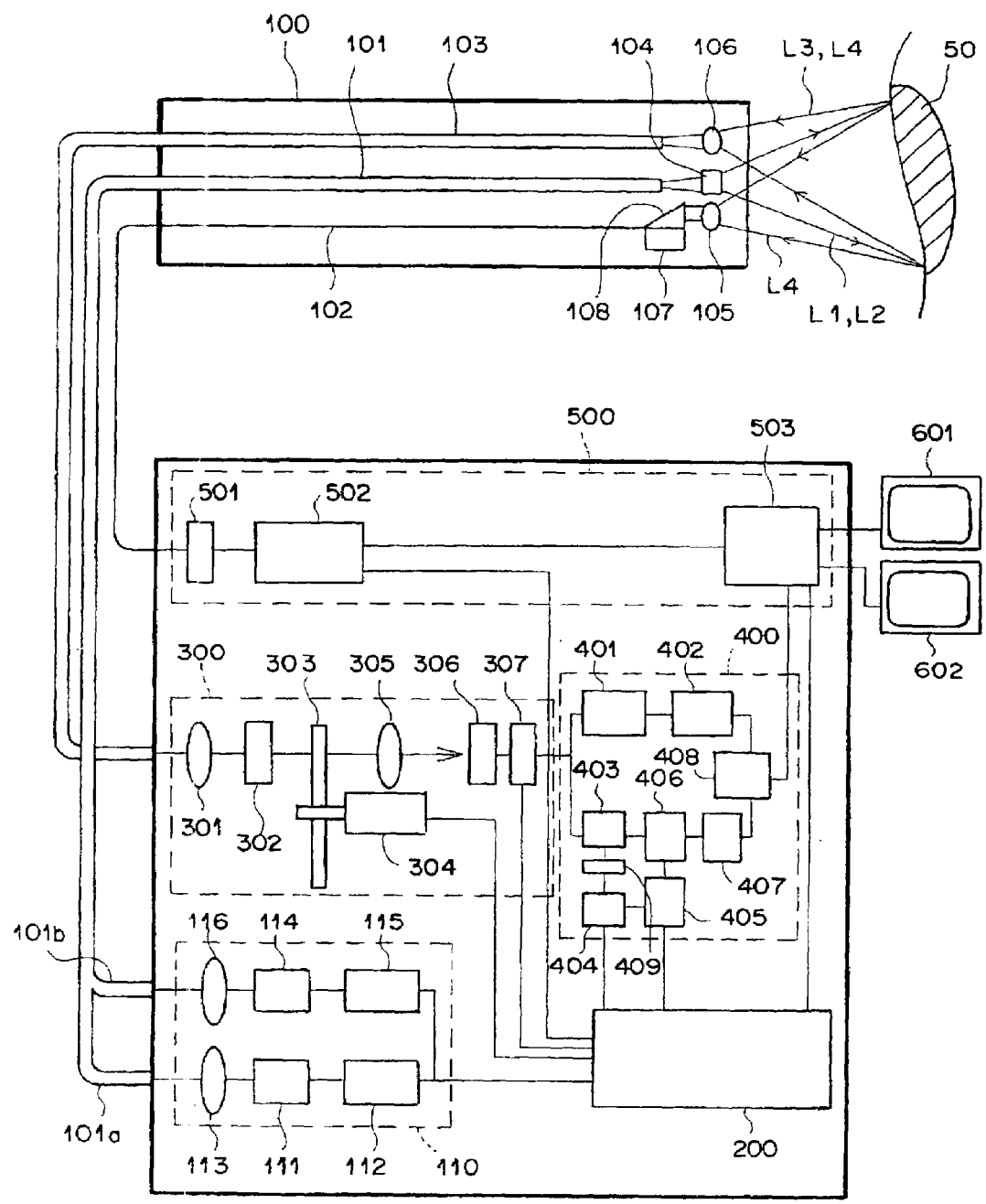
FIG. 6 is a schematic drawing of a fluorescent endoscope apparatus according to the second embodiment of the present invention.

Next, the second embodiment of a fluorescent endoscope apparatus, as shown in FIGS. 5 and 6, implementing the fluorescent-light image obtaining apparatus according to the present invention will be explained. FIG. 6 is a schematic drawing of a fluorescent endoscope apparatus implementing the fluorescent-light image obtaining apparatus according to the present invention. Note that for the current embodiment, the components shared in common with the first embodiment are labeled with the same reference numerals, and where further explanation thereof is not particularly required, it has been omitted.

The fluorescent endoscope apparatus according to the second embodiment comprises an endoscope insertion portion 100 to be inserted into the body of a patient near the position at which the primary nidus of a disease and areas of suspected secondary infection are located, an illuminating unit for emitting normal-image and IR reflected-light image obtaining-use white-light and fluorescent-light image obtaining-use stimulating-light, a image obtaining unit 300 for obtaining two types of fluorescent-light images having different wavelength bands and a reflected-light image, a composite-image forming unit 400 for computing a division value between the fluorescent-light images, assigning a hue to a computed-image based on the division value and forming a tissue-state image, assigning a luminosity V to the pixel values of an IR reflected-light image and forming a tissue-state image, and combining each of said two tissue-state images to form a composite-image, an image processing unit 500 for performing the image processing required in order to display the normal-image and the composite-image as a visible image, a control computer 200, which is connected to each of the units, for controlling the operation timing thereof, a monitor 601 for displaying as a visible image the normal-image data processed by the image processing unit 500, and a monitor 602 for displaying the composite-image processed by the image processing unit 140 as a visible image.

The image obtaining unit 300 comprises a stimulating-light cutoff filter 302 for cutting off light in the wavelength band below 420 nm, which is close to the wavelength band of the stimulating-light, from the fluorescent light L3 passing through the image fiber 103, a switching filter 303 composed of a combination of three types of optical filters, a filter rotating apparatus 304 for rotating said switching filter 303, a CCD photographing element 306 for obtaining a fluorescent-light image passing through said switching filter 303 or an IR reflected-light image, and an A/D converting circuit 307 for digitizing the signal obtained by the CCD photographing element 306.

The switching filter 303, which is the same as in the first embodiment, is formed of three types of optical filters: an optical filter 303a, which is a wide-band fluorescent-light image band-pass filter for transmitting light in the 430-730 nm wavelength range, an optical filter 303b, which is a narrow-band fluorescent-light image band-pass filter for transmitting light in the 430-530 nm wavelength range, and an optical filter 303c, which is an IR reflected-light image band-pass filter for transmitting light in the 750-900 nm wavelength range.

The image composing unit 400 comprises fluorescent-light image memory 401 for storing the digitized fluorescent-light image signal data of the fluorescent-light image composed of two different wavelength bands, an IR reflected-light image memory 403 for storing the IR reflected-light image signal data, a tissue-state image forming means 402 for performing computations according to the ratio of each pixel value of the fluorescent-light image composed of two different wavelength bands stored in the fluorescent-light image memory 401 and assigning a hue H to the computed value of each pixel value and forming a tissue-state image, a bit shifting means 409 for shifting the bit value of each pixel value represented by 9 bits of data or more from among the pixel values of the IR reflected-light image stored in the IR reflected-light image memory 403 so that each pixel value is represented by data of 8 bits or less, a statistical-quantity computing means 404 provided with an 8 bit statistical quantity calculator for computing a predetermined statistical quantity of each pixel value output from the bit shifting means 409, a coefficient computing means 405 for computing a predetermined coefficient based on the statistical quantity output from the statistical-quantity computing means 404, a coefficient multiplying means 406 for multiplying each pixel value of an IR reflected-light image by the predetermined coefficient output from the coefficient computing means 405, a tissue-form image forming means 407 for assigning a display gradation of a luminosity V to each pixel value output from the coefficient multiplier computing means 406 and forming a tissue-form image, and a composite-image forming means 408 for combining and outputting as a composite-image the tissue-state image output from the tissue-state image forming means 402 and the tissue-form image output from the tissue-form forming means 407. Note that according to the current embodiment, the fluorescent-light image data having two different wavelength bands is stored in the fluorescent-light image memory 401 and the IR reflected-light image data is stored in the IR reflected-light image memory 403, however, the fluorescent-light image memory and the IR reflected-light image memory can be made to be a common memory for storing both types of image data. In such a case, the common memory can comprise a narrow-band fluorescent-light image memory zone, a wide-band fluorescent-light image memory zone and an IR reflected-light image memory zone, and a fluorescent-light image transmitted by the optical filter 303a is stored in the wide-band fluorescent-light memory zone, a fluorescent-light image transmitted by the optical filter 303b is stored in the narrow-band fluorescent-light image memory zone, and an IR reflected-light image transmitted by the optical filter 303c is stored in the IR reflected-light image memory zone.

The image processing unit 500 comprises an A/D converting circuit 501 for digitizing the normal-image obtained by the CCD photographing element 107, a normal-image memory 502 for storing the digitized normal-image, and a video signal processing circuit 503 for converting to a video signal the image signal output from said normal-image memory 502 and the composite-image output by the composite-image forming means 408.

Next, the operation of a fluorescent endoscope apparatus of the configuration described above and implementing the fluorescent-light image display apparatus according to the present invention will be described. According to the fluorescent endoscope of the current embodiment, in the same way as in the first embodiment, the obtaining of a normal-image and an IR reflected-light image, and the obtaining of a fluorescent-light image can be performed alternately in a time division manner; however, because the operation occurring when a fluorescent-light image is obtained and the operation occurring when a normal-image and an IR reflected-light image are to be obtained are the same as in the embodiment described above, an explanation thereof has been omitted, and the operation occurring when a composite-image is to be formed, which is different from that occurring in the first embodiment described above, is explained.

The wide-band fluorescent-light image and the narrow-band fluorescent-light image that have been obtained by the CCD photographing element 306 of the image obtaining unit 300 and digitized are stored in the fluorescent-light image memory 401. Note that the wide-band fluorescent-light image that has been obtained by the CCD photographing element 306 is stored in the wide-band fluorescent-light image memory zone (not shown) of the fluorescent-light memory 401 and the narrow-band fluorescent-light image that has been obtained by the CCD photographing element 306 is stored in the narrow-band fluorescent-light memory zone (not shown) thereof. Then, the IR reflected-light image obtained by the same CCD photographing element 306 of the image obtaining unit 300 is stored in the IR reflected-light image memory 403.

In the same way as occurred in the first embodiment described above, the tissue-state image forming means 402 computes the ratio of each pixel value of the narrow-band fluorescent-light image to the corresponding pixel value of the wide-band fluorescent-light image, each image being stored in the fluorescent-light image memory 401, and forms a computed-image is formed. A hue H is assigned to the pixel values of said computed-image, and a tissue-state image is formed and output. Further, after all pixel values of the IR reflected-light image stored in the IR reflected-light image memory 403 represented by data of 9 bits or more are bit shifted so that each pixel value is represented by data of 8 bits or less by the bit shifting means 409, all of the pixel values are output to the statistical-quantity computing means 404, and the statistical-quantity computing means 404 computes the average value M and the standard deviation σ of each pixel value. Then, the average value M and the standard deviation σ are output to the coefficient computing means 405. The coefficient C is determined by the coefficient computing means according to the formula (2) below. Each pixel value of the IR reflected-light image is multiplied by the coefficient C by the coefficient multiplying means 406, and each computed value of each pixel is output to the tissue-form image forming means 407. The tissue-form image forming means 407 assigns a display gradation of the brightness to the computed value of each pixel, and forms and outputs a tissue-form image.

$$\text{Upper limit of the display gradation of the brightness} \times a \approx (m+b+\sigma) \times c \quad (2)$$

In the same way as in the first embodiment, the tissue-state image output from the tissue-state image forming means 402 and the tissue-form image output from the tissue-form image forming means 407 are combined and output by the composite-image forming means 408.

The composite-image converted to a video signal by the video signal processing circuit 503 is input to the monitor 602 and displayed thereon as a visible image. The continuous operation described above is controlled by the control computer 150. Note that other operations are the same as those occurring in the first embodiment.

In addition, regarding the operation occurring when a tissue-state image and a tissue-form image are to be formed, the processing can be carried out in a series of operations wherein the tissue-state image is formed, and then, after the tissue-form image is formed, the two images are combined, or alternatively, in parallel operations wherein the tissue-state image and the tissue-form image are formed at the same time, after which the two images are combined. When the processing is performed in a parallel series, the operation can be completed faster.

Further, it is desirable that the gradation processing occurring in the second embodiment be capable of being switched ON/OFF.

Still further, according to the second embodiment, although an average value and a standard deviation have been computed as a statistical quantity from the pixel values of an IR reflected-light image and a predetermined coefficient has been computed, for cases in which a combination of the largest pixel value and the smallest pixel value is used as a statistical quantity, a coefficient c can be obtained as in the formula (3), for example. Given the largest pixel value max, the smallest pixel value min, a coefficient c by which an IR reflected-light image is to be multiplied, and desired constants a,b:

$$\text{The upper limit of the display gradation of the brightness} \times a \approx ((\max+\min)/2 + b \times (\max-\min)/2) \times c \quad (3)$$

In addition, according to the second embodiment, it is feasible that the statistical quantity computed by the statistical quantity computing means 404 not be based on an IR reflected-light image obtained in real-time in the same frame, and can be based on an IR reflected-light image obtained in the previous frame.

According to the fluorescent endoscope apparatus of the second embodiment of the present Invention, because a statistical value of the pixel values of an IR reflected-light image is computed and a display gradation of the brightness is assigned based on said statistical quantity, even for cases in which the pixel values of an image to which brightness data are small, a composite-image already having a brightness above a predetermined value can be formed, and also, because the dynamic range of the display gradation of the brightness data can be virtually expanded, a composite-image already capable of visual recognition can be provided. Further, for cases in which an endoscope, etc., that is to be inserted into the body of a patient is used, even when stimulating-light emitting end of the endoscope insertion portion is located a far distance from the target area, because a composite-image already having a brightness above a predetermined value can be formed, composite-images facilitating visual recognition across a wide measurement-distance range can be provided.

Next, the third embodiment of a fluorescent endoscope apparatus implementing a fluorescent-light image obtaining apparatus implementing the fluorescent-light image display method according to the present invention will be explained. The forming of a tissue-state image occurring in the first and second embodiments described above, wherein a hue H is assigned to a computed-image based on the ratio between the narrow-band fluorescent-light image and the wide-band fluorescent-light image, is performed so that a saturation S is assigned to the computed-image and a tissue-state image is formed, and said tissue-state image is combined with the IR reflected-light image to form a composite-image, which is then displayed. The forming of the tissue-form image is performed in the same way as in the first and second embodiments described above, that is, a luminosity V is assigned to a reflected-light image and a tissue-form image is formed. When the composite-image formed according to the current embodiment is displayed based on the three color attributes, the image is displayed with the colors within the color range show in the perspective view of FIG. 7. That is to say, for example, when the hue is green (an appropriate hue can be used): for a normal tissue located at a position in which the distance from the stimulating-light emitting end of the endoscope insertion portion to the target area is close, the green is displayed bright and vivid; for a normal tissue located at a position wherein said distance is far, the green is displayed dark and vivid; for a diseased tissue located at a position wherein said distance is close, the toneless bright white is displayed; and for a diseased tissue located at a position wherein said distance is far, the toneless black is displayed. Other structures and operations are the same as those occurring in the first or second embodiments.

Further, according to the first through third embodiments, although the white-light source 111 is a multi-purpose light source for emitting both normal-image use white-light and reference light, a configuration in which a separate light source is provided for each respective type of light can also be adopted.

Still further, although in the first through the third embodiments a computed-image has been computed based on the ratio between the narrow-band fluorescent-light image and the wide-band fluorescent-light image, the computed-image can also be computed based on the ratio of the narrow-band fluorescent-light image and the reflected-light image. Further, the use of a computed-image can be forgone, and a hue or saturation assigned to the fluorescent-light image itself.

In addition, the CCD photographing element is a multi-purpose obtaining element for obtaining fluorescent-light images and reflected-light images, however, a separate obtaining element for obtaining each type of image may also be provided. Also, a separate CCD photographing element can be provided for obtaining the wide-band fluorescent-light images and the narrow-band fluorescent-light images, respectively. By providing separate CCD photographing element s in this way, it becomes possible to photograph the images in parallel, and it is not necessary to photograph them in a time series manner.

Figure 8:
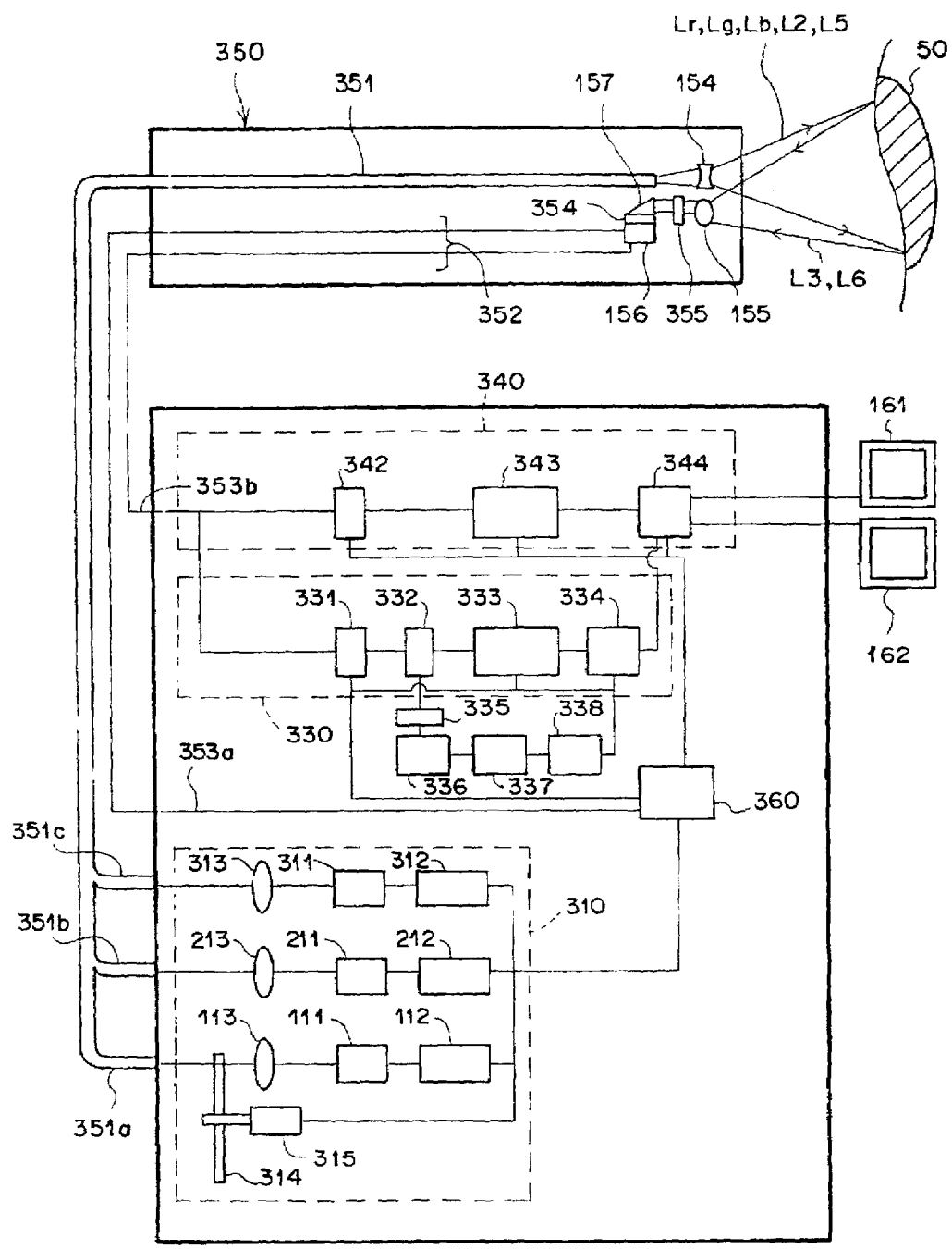
FIG. 8 is a schematic drawing of a fluorescent endoscope apparatus according to the fourth embodiment of the present invention, FIG. 9 schematically shows a mosaic filter.

Next, the fourth embodiment of a fluorescent endoscope apparatus implementing the fluorescent-light image obtaining apparatus according to the present invention will be explained. FIG. 8 is a schematic drawing of a fluorescent endoscope apparatus according to the fourth embodiment of the present invention.

According to the fluorescent endoscope apparatus according to the current embodiment, a normal-image is obtained by a CCD photographing element 156 of the reflected-light reflected from a target area upon irradiation thereof by an area-order light (Lr, Lg, Lb), and the normal-image is displayed on a monitor 161. At the same time, a narrow-band fluorescent-light image and a wide-band fluorescent-light image are obtained by a CCD photographing element 156 based on the fluorescent-light emitted from a target area upon irradiation thereof by a stimulating-light, and based on the division value of both of said fluorescent-light images pairs of chromaticity coordinates (x,y) occurring in the XYZ color specification system are assigned thereto and a tissue-state image is formed. An IR reflected-light image is obtained of the reflected-light reflected from a target area upon irradiation thereof by a reference-light and a saturation Z is assigned thereto based on the pixel values thereof, and a tissue-form image is formed. A composite-image based on the tissue-state image and the tissue-form image is displayed on a monitor 162.

The fluorescent endoscope apparatus according to the fourth embodiment comprises: an endoscope insertion portion 350, provided with a CCD photographing element 156 at the forward end thereof, to be inserted into the body of a patient where the primary nidus and suspected areas of secondary infection are located; an illuminating unit 310 for emitting area-order light (red light Lr, green light Lg, blue light Lb), which is normal-image obtaining-use illuminating light, stimulating-light L2, which is fluorescent-light image obtaining-use stimulating-light, and reference light L5, which is IR reflected-light image obtaining-use reference light; a composite-image forming unit 330 for computing a division value between said fluorescent-light images, assigning a chromaticity (hue and saturation) to a computed-image based on said division value and forming a tissue-state image, for assigning a brightness Z to the pixel values of the IR reflected-light image and forming a tissue-form image, and for combining the tissue-state image and the tissue-form image to form a composite-image; an image processing unit 340 for performing image processing in order to display the normal-image and the composite-image as visible images; a control computer 360 connected to each unit and controlling the operation timing thereof; a monitor 161 for displaying as a visible image the normal-image processed by the image processing unit 340; and a monitor 162 for displaying as a visible image the composite-image processed by the image processing unit 340.

The endoscope insertion portion 350 comprises a light guide 351 extending to the forward end thereof and a CCD cable 352, and an objective lens 155 is provided at the forward end of the CCD cable 352. A CCD photographing element 156 having a non-chip mosaic filter 354 composed of a group of microscopic band-filters is connected to the forward end of the CCD cable 352, and a prism 157 is attached to said CCD photographing element 156.

The light guide 351 is an integrated cable containing a light guide 351*a* for the area-order guide, a stimulating-light use light guide 352*b*, and a reference-light use light guide 351*c* bundled together, and each of said light guides is connected to the illuminating unit 310.

The CCD cable 352 is includes an activation line 353*a* for transmitting the CCD photographing element activation signal and an output line 353*b* for reading out the signal from the CCD photographing element 156; one end of the activation line 353*a* is connected to the control computer 360, and one end of the output line 353*b* is connected to the composite-image forming unit 330 and the image processing unit 340.

Figure 9:
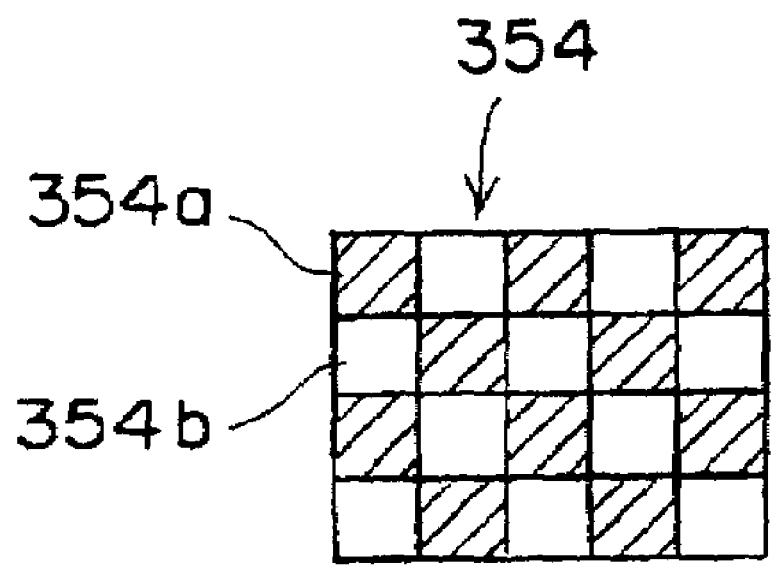

The mosaic filter 354, as shown in FIG. 9, is composed of narrow-band filters 354*a* for transmitting light in the 430-530 nm wavelength band and all-wavelength band filters 354*b* for transmitting light of all wavelengths, grouped alternately thereon, and each of the narrow-band filters is in a one-to-one correspondence to the pixels of the CCD photographing element 156.

The illuminating unit 310 comprises a white-light source 111 for emitting white-light and a white-light source use power source 112 electrically connected to said white-light source 111, a switching filter 314 for switching in order to separate the white-light into R-light Lr, G-light Lg, and B-light Lb, a filter rotating portion 315 for rotating the switching filter 314, a GaN type semiconductor laser 211 for emitting fluorescent-light image obtaining-use stimulating-light L2 and a semiconductor-laser use power source 212 electrically connected to said GaN semiconductor laser 211, a reference-light source 311 which is a semiconductor laser for emitting IR reflected-light image obtaining-use reference light L5 and a semiconductor-laser use power source 312 electrically connected to said reference-light source 311.

Figure 10:
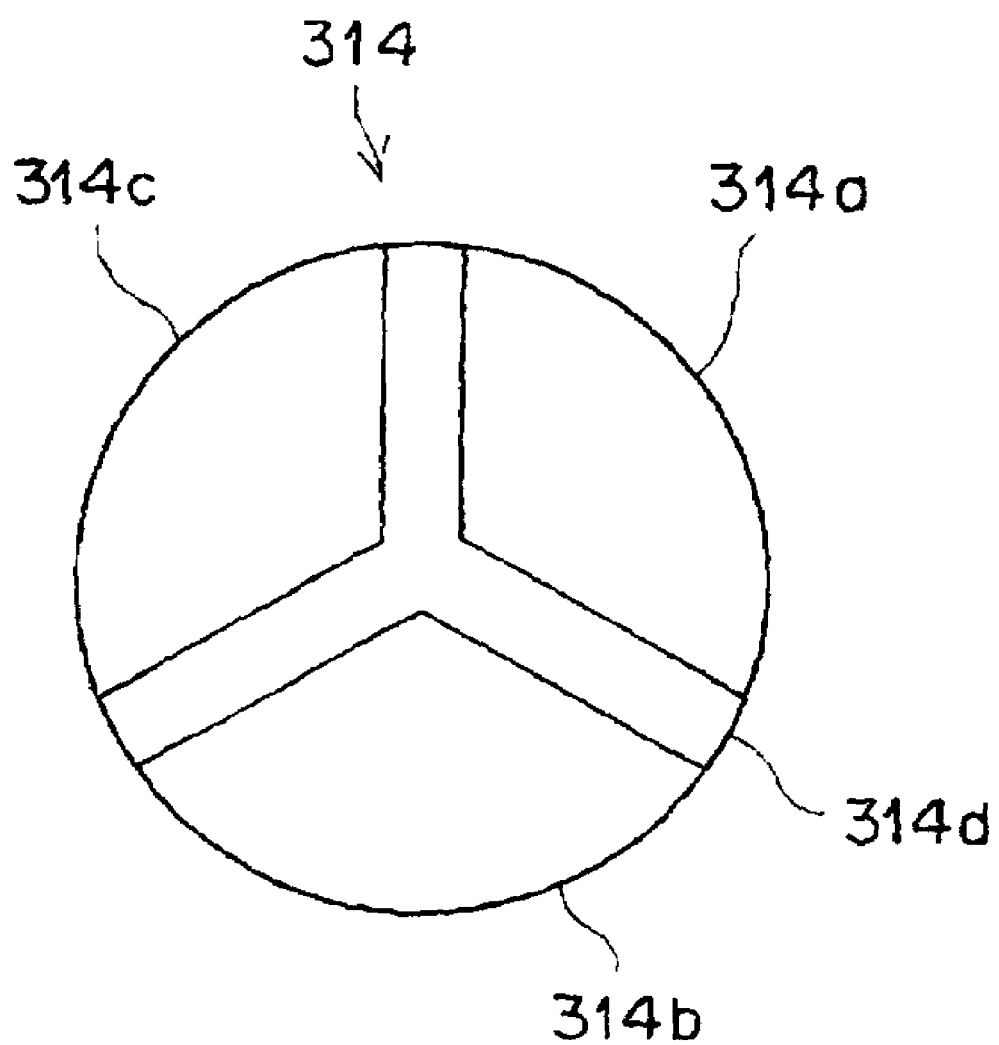
FIG. 10 is a schematic drawing of the switching filter used in the fourth embodiment.

The switching filter 314, as shown in FIG. 10, is provided with a R light transmitting R filter 314*a*, a G light transmitting filter 314*b*, a B light transmitting filter 314*c*, and a mask portion 314*d* having a light-cutoff function.

The composite-image forming unit 330 comprises: an A/D converting circuit 331 for digitizing the image signal obtained by the CCD photographing element 156 when a target area is irradiated by stimulating-light L2 or reference light L5; and image memory 332 composed of different memory zones for storing a narrow-band fluorescent-light image received at the pixels corresponding to the narrow-band filter 354*a* of the mosaic filter when the stimulating-light L2 is emitted, a wide-band fluorescent-light image received at the pixels corresponding to the all-wavelength bands filter 354*b* of the mosaic filter when the stimulating-light L2 is emitted, and a reflected-light image received at the pixels corresponding to the all -wavelength bands filter 354*b* of the mosaic filter when the reference light L5 is emitted; a tissue-state image forming means 333 for computing a division value between a narrow-band fluorescent-light image and a wide-band fluorescent-light image at the adjacent pixels stored in the image memory 332 and assigning a pair of chromaticity coordinates (x,y) to the computed value of each pixel, and forming a tissue-state image; a bit shifting means 335 for shifting the pixel value of each pixel among the pixels of an IR reflected-light image stored in the image memory 332 that is represented by data of 9-bits or more to data of 8-bits or less; a statistical-quantity computing means 336 provided with an 8-bit statistical quantity calculator for computing a predetermined statistical quantity for each pixel value output from the bit shifting means 335; a gradation processing function determining means 337 for determining a gradation processing function based on the statistical quantity output from the statistical-quantity computing means 336; a tissue-form image forming means 338 for assigning a display gradation of the brightness Z, based on the gradation processing function output from the gradation processing function determining means 337, to each pixel value of the IR reflected-light image and forming a tissue-form image; and a composite-image forming means 334 for combining the tissue-state image output from the tissue-state image forming means 333 and the tissue-form image output from the tissue-form image forming means 338 to form a composite-image.

Figure 2:
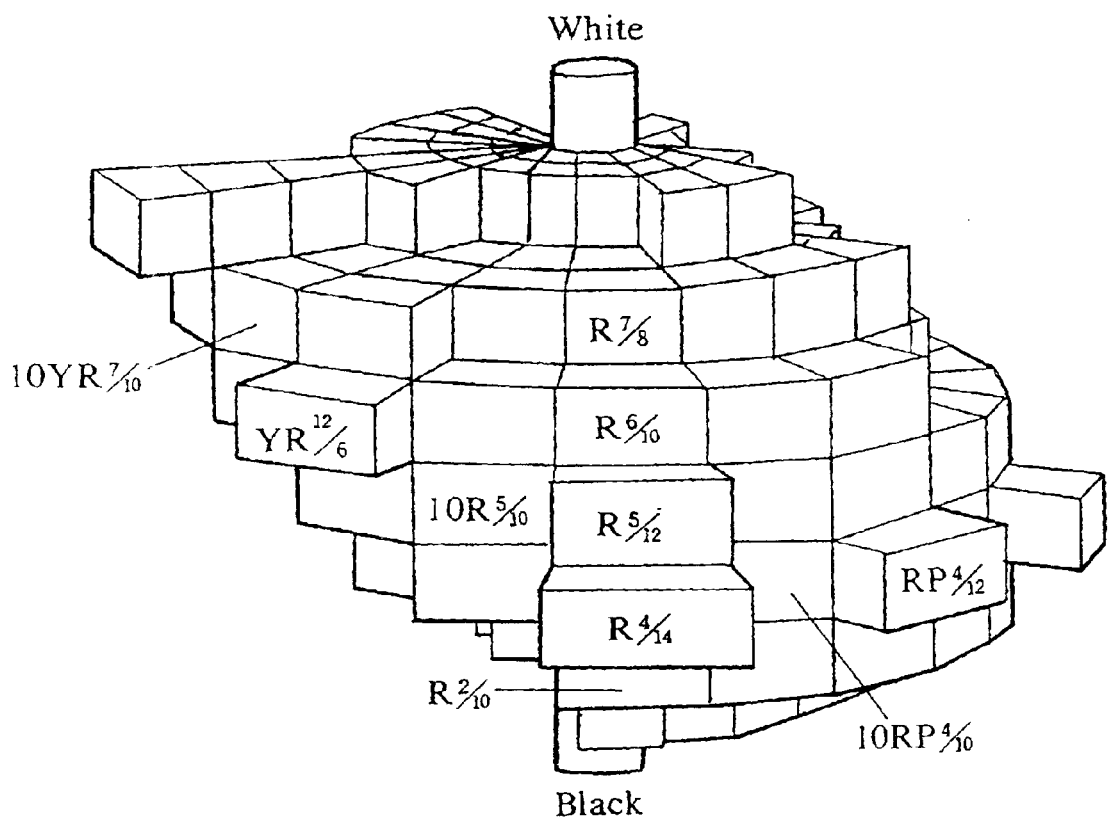
FIG. 2 is a drawing provided for explanation of a three-dimensional Munsell color diagram.
Figure 3:
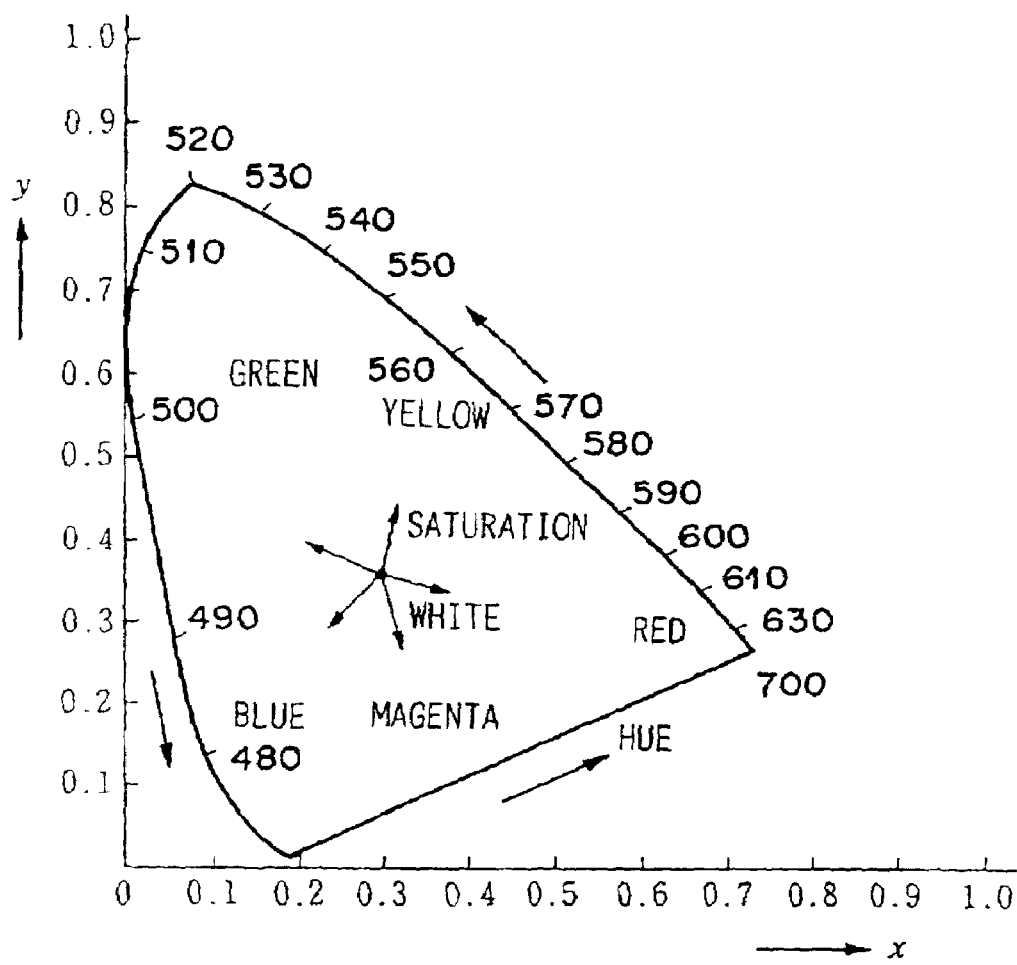
FIG. 3 is an XYZ color specification system chromaticity graph.

A lookup-table correlating the division values of fluorescent-light images and the chromaticity coordinates (x,y) occurring in the XYZ color specification system has been pre-recorded in the tissue-state image forming means 333. In this lookup-table, aforementioned division value, which has been converted to a 16-bit value having no reference number, and the chromaticity coordinates (x,y) shown in FIG. 3, which are the coordinates of a spectra locus of red (650 nm), yellow and green (520 nm) range, are correlated as shown in Table 2.

TABLE 2

| Division Value | 0 | 1 | 2 | ... | 65535 |
|---|---|---|---|---|---|
| Wavelength | 520.0 nm | | | ... | 650.0 nm |
| Chromaticity | x = 0.0743 | | | ... | x = 0.7260 |
| | y = 0.8338 | | | | y = 0.2740 |

The image processing unit 340 is provided with an A/D converting circuit 342 for digitizing the image signal corresponding to the pixels of the wide-band filter 354b of the mosaic filter 354 when R-light Lr, G-light Lg or B-light Lb is irradiated, a normal-image memory 343 for storing each color of a digitized normal-image, a video signal processing circuit 344 for converting to a video signal the three-color image signals of matched phases read out from said normal-image memory 343 when a normal-image is to be displayed and outputting said video signal, and also for converting to a video signal the composite-image output from the composite-image forming unit 330 when a fluorescent-light image is to be displayed and outputting said video signal.

Next, the operation of the fluorescent endoscope according to the current embodiment described above will be explained. According to the fluorescent endoscope apparatus of the current embodiment, the obtaining of a normal-image, an IR reflected-light image, and a fluorescent-light image is performed in a time-division manner, and a normal-image is displayed on the monitor 161 and a composite-image based on the fluorescent-light L3 and the reflected-light L4 is displayed on the monitor 162. In order to obtain each image in a time division manner, the red light Lr, green light Lg, blue light Lb, stimulating-light L2 and reference light L5 are emitted from the illuminating unit in order.

First, the operation occurring when a fluorescent-light image and an IR reflected-light image are to be obtained, and a composite-image is to be formed based on both of said images and displayed will be explained. When obtaining a fluorescent-light image, based on a signal from the control computer 350, the semiconductor-laser use power source 212 is activated and stimulating-light L2 having a wavelength of 410 nm is emitted from the GaN-type semiconductor laser 211. The stimulating-light L2 is transmitted by a lens 213 and enters the stimulating-light use light guide 351b, and after being guided to the stimulating-light emitting end of the endoscope insertion portion, the stimulating-light L2 is projected onto a target area 50 by an illuminating lens 154.

The fluorescent-light emitted from the target area upon irradiation thereof by the stimulating-light L2 is focused by a focusing lens 155, reflected by a prism 157, transmitted by the mosaic filter 354 and focused on the CCD photographing element 156 as a fluorescent-light image. Because the reflected stimulating-light L2 occurring at this time id cutoff by a stimulating-light cutoff filter 355, it does not enter the CCD photographing element 156.

The image signal photoelectrically converted by the CCD photographing element 156 is digitized by the A/D converting circuit 331 of the composite-image forming means 330, separated into a narrow-band fluorescent-light image transmitted by the narrow-band filter 354a and a wide-band fluorescent-light image transmitted by the wide-band filter 354b, and each of said fluorescent-light images are stored in the corresponding memory zones of the image memory 332.

Next, the operation for obtaining an IR reflected-light image when reference-light L5 is emitted will be explained. Based on a signal from the control computer 350, the reference-light use power source 312 is activated and reference-light L5 is emitted from the reference-light source 311. The reference-light L5 is transmitted by a lens 313 and enters the reference-light use light guide 351c, and after being guided to the stimulating-light emitting end of the endoscope insertion portion, the reference-light L5 is projected onto a target area 50 by an illuminating lens 154.

The reflected-light L6 reflected by the target area 50 upon irradiation thereof by the reference-light L5 is focused by the focusing lens 155, reflected by the prism 157, transmitted by the mosaic filter 354, and focused on the CCD photographing element 156 as an IR reflected-light image. Of the image signal photoelectrically converted by the CCD photographing element 156, only the signal of the light received at the pixels corresponding to the all-wavelength bands filter 354b is digitized by the A/D converting circuit 331 of the composite-image forming unit 330 and stored in a different memory zone of the image memory 332 from the fluorescent-light images described above as an IR reflected-light image.

Regarding the narrow-band fluorescent-light image and wide-band fluorescent-light image stored in the image memory 332, each pixel value of the narrow-band fluorescent-light image is divided by the corresponding pixel value of the wide-band fluorescent-light image, and the division value of each pixel□is converted to a 16-bit data not having a reference number. Then, a pair of chromaticity coordinates occurring in the XYZ color specification system is assigned to each pixel referring to the pre-recorded lookup-table, and a tissue-state image is formed and output to the composite-image forming means 233.

Further, after the IR reflected-light image stored in the image memory 332 has been subjected to bit shifting by the bit shifting means 335, the average value M and the standard deviation σ of each pixel value are computed by the statistical-quantity computing means 336. Then, the average value M and the standard deviation σ are output to the gradation processing function determining means 337. If the gradation processing function is designated as f(x) before the change, the gradation processing function determining means changes and determines the gradation processing function by rewriting f(x) such that f(x−Min/(Max−Min)) (here, Min=m−b×σ, Max=m+b×σ).

The tissue-form image forming means 338 assigns, based on said changed gradation processing function, a display gradation of a brightness Z occurring in the XYZ color specification system to each pixel value of the IR reflected-light image and forms a tissue-form image, and outputs said formed tissue-form image.

Then, the composite-image forming means 334 combines the tissue-state image and the tissue-form image based on the brightness Z to form a composite-image. When forming a composite-image, first, the chromaticity coordinates (x,y), the brightness Z, and from the formula, X, Y, and Z are obtained:

$$x=X/(Y+Y+Z)$$

$$y=Y/(Y+Y+Z)$$

$$z=Z/(Y+Y+Z)$$

Afterwards, using the formula, the RGB is converted and the composite-image is formed and output to the video signal processing circuit 344:

$$R=0.41844X-0.15866Y-0.08283Z$$

$$G=0.09117X+0.25242Y+0.01570Z$$

$$B=0.00092X=0.00255Y-0.17858Z$$

The composite-image converted to a video signal by the video signal converting circuit 344 is input to the monitor 162 and displayed thereon as a visual image. The continuous operation described above is controlled by the control computer 360.

First, the target area 50 is irradiated with R light Lr, and the reflected R light Lr reflected form the target area 50 is focused on the CCD photographing element 156 as a R light reflected-light image. The R-light image signal received at the pixels corresponding to the all-wavelength bands filter 354, from among the signal output from the CCD photographing element 156, is digitized by the A/D converting circuit and stored in the R-light image signal memory zone of a normal-image memory 343. Subsequently, by the same operation, a G-light image signal and a B-light image signal are obtained, and each is stored in the G-light image signal memory zone and the B-light image signal memory zone of the normal-image memory, respectively.

After the three colored image signals is stored in the normal-image memory 343, the three colored image signals are output with matched phases and timings to the video signal processing circuit, where they are converted to a video signal. The video signal is output to the monitor 161 and displayed thereon as a color image.

Note that as an alternative version of the fourth embodiment described above, when forming a composite-image, instead of using a lookup-table recording the chromaticity coordinates (x,y) corresponding to the division value between the fluorescent-light images to determine a pair of chromaticity coordinates (x,y), it is also possible to use a lookup-table correlating hues in the range of Red (650 nm), and Yellow and Green (520 nm) with the 16-bit data having no reference number representing a pixel value of each fluorescent-light image, as shown in Table 3, to assign a pair of chromaticity coordinates (x,y).

TABLE 3

| | | Intensity of Narrow-Band Fluorescent-Image | | | |
|---|---|---|---|---|---|
| | | 0 | 1 | 2 | ... 65535 |
| Intensity of Wide-Band Fluorescent-Image | 0 | x = 0.0743 y = 0.8338 | | | |
| | 1 | ... | x = 0.0743 y = 0.8338 | | |
| | 2 | ... | ... | x = 0.0743 y = 0.8338 | |
| | ... | ... | ... | ... | ... ... |
| | 65535 | x = 0.7260 y = 0.2740 | ... | ... | ... x = 0.0743 y = 0.8338 |

Note that according to the current embodiment, although a pair of chromaticity coordinates (x,y) occurring in the XYZ color specification system has been assigned to the IR reflected-light image and a tissue-state image formed, it is also possible to use a color difference signal as the color data. In this case, if a color difference signal IQ is assigned to a computed-image and a tissue state image is formed and a brightness signal Y is assigned to an IR reflected-light image and a tissue-form image is formed, because a color difference signal IQ determined from the tissue-state image and a brightness signal Y determined from the IR reflected-light image can be input directly into the video signal processing circuit 344, the necessity to form an RGB signal is eliminated, and the configuration of the apparatus can be simplified.

Next the operation occurring when a normal-image is to be displayed will be explained. Because the operation for cases other than obtaining a normal-image in a time division manner are substantially the same as that occurring in the first embodiment, mainly, portions of the operation that differ will be explained.

Figure 11:
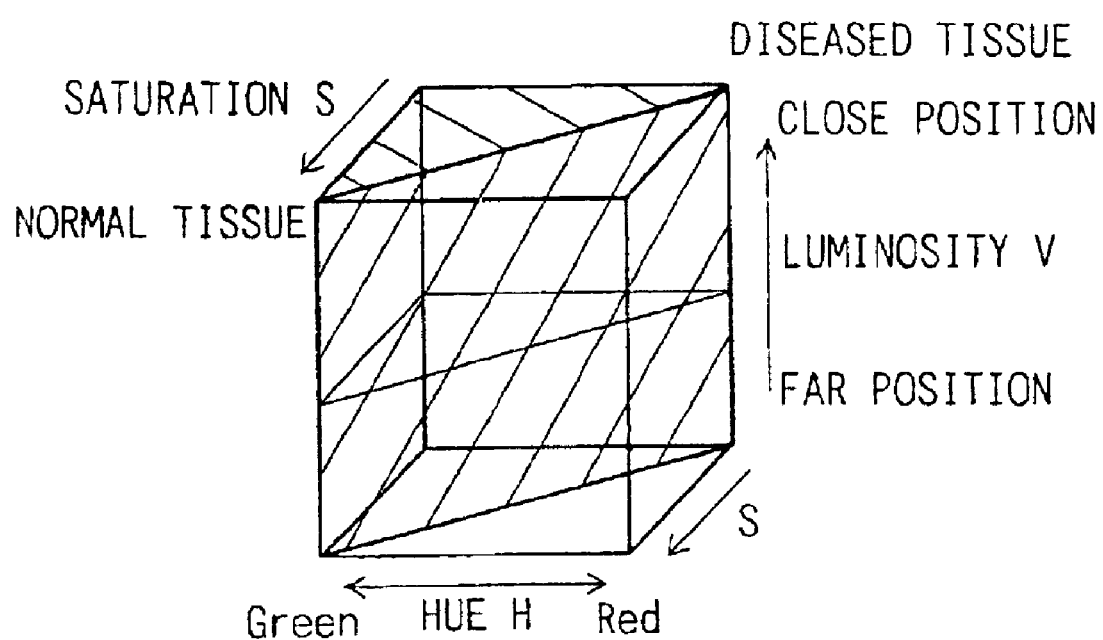
FIG. 11 shows the color range of a composite-image displayed by a fluorescent endoscope apparatus according to the fourth embodiment of the present invention.

In addition according to the fourth embodiment described above, although an XYZ color spaced has been used as the color space, an HSV color space can be used as the color space; for example, for cases in which a hue and a saturation are assigned to a computed-image and a tissue-state image is formed, a composite-image will be displayed according to the range of colors shown in the perspective potion of FIG. 11. That is to say: a normal tissue in a target that is located at a close distance from the stimulating-light emitting end of the endoscope insertion portion 100 will be displayed as a bright, vivid green; when said distance is far, a normal tissue is displayed as a dark, vivid green; a diseased tissue is displayed as a bright toneless red when said distance is close; and a diseased tissue is displayed as a dark, toneless red when said distance is far. Further, regarding the assigning of a saturation, a method the opposite of that described above can be applied, that is, a low saturation can be assigned to a normal tissue and a high saturation can be assigned to a diseased tissue. In this case, when diagnosis is performed, a diseased tissue can be more accurately detected.

Further, it is desirable that the gradation processing occurring in the fourth embodiment described above is capable of being switched ON/OFF.

Still further, according to the fourth embodiment, although an average value and a standard deviation have been computed from the pixel values of an IR reflected-light image, as statistical quantity, and the gradation processing function changed, for cases in which a combination of the largest pixel value and the smallest pixel value are used, the gradation processing function can be rewritten such that, for example, given the largest pixel value max, the smallest pixel value min of the pixel values of an IR reflected-light image, and desired constants α and β:

$$\approx (max+min)/2 + \alpha \times (max-min)/2$$

is the lower limit of the display gradation of the brightness, and $$(max+min)/2 - \beta \times (max-min)/2$$

is the upper limit of the display gradation of the brightness.

Figure 12:
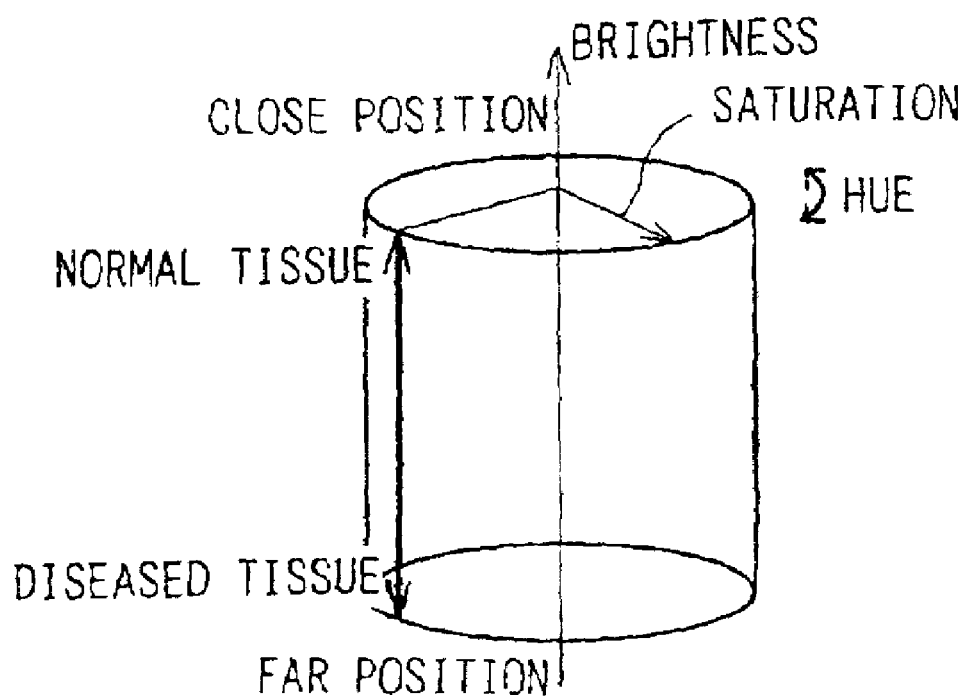
FIG. 12 is a schematic drawing of a fluorescent endoscope apparatus according to the fifth embodiment of the present invention.
Figure 14:
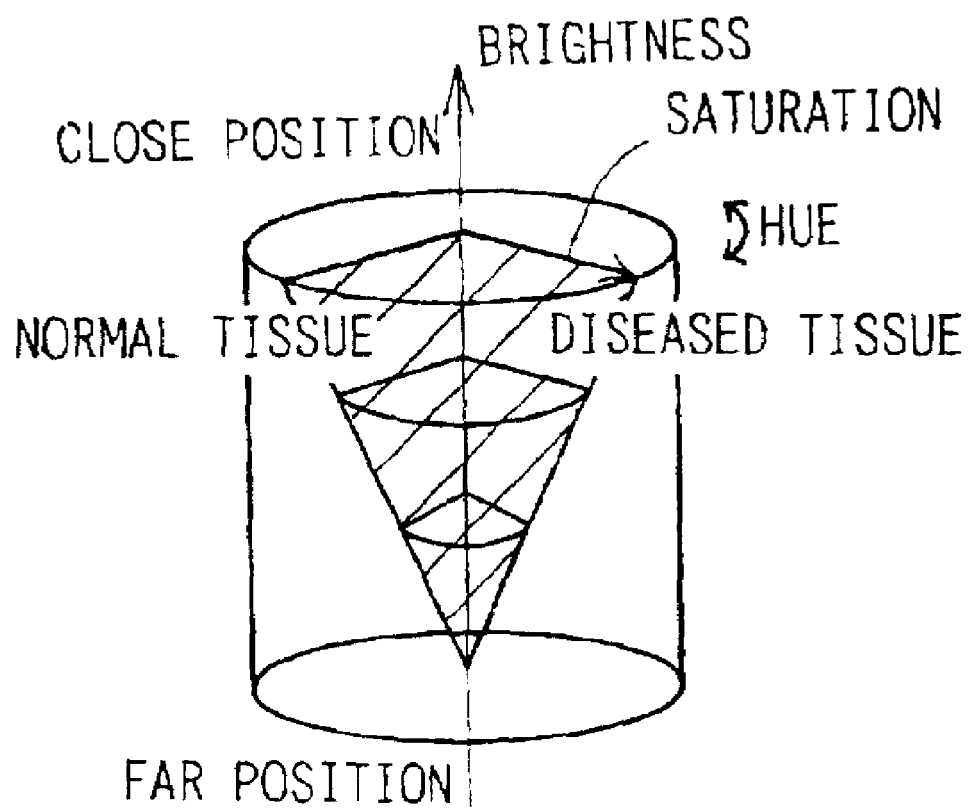
FIG. 14 shows the color range of a composite-image displayed by a fluorescent endoscope apparatus according to the sixth embodiment of the present invention.
Figure 15:
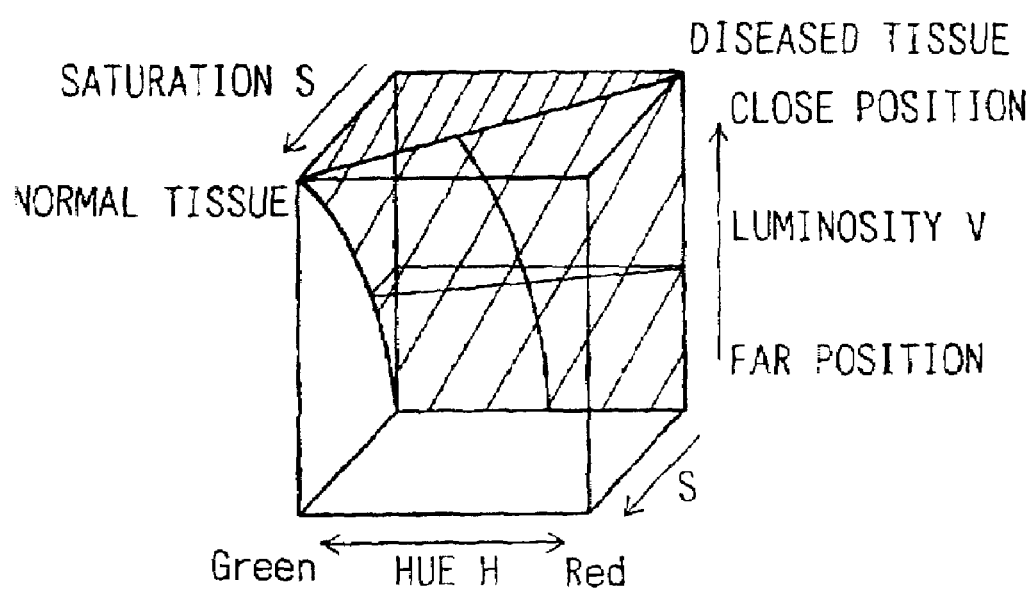
FIG. 15 shows the color range of a composite-image displayed by a fluorescent endoscope apparatus according to the seventh embodiment of the present invention.

Next, a fifth embodiment of a fluorescent endoscope apparatus implementing the fluorescent-light image display apparatus according to the present invention will be explained. According to the current embodiment, the forming of a tissue-state image occurring in the first through the fourth embodiments, wherein a hue H or chromaticity (hue and saturation) have been assigned to a computed-image based on the division value between a narrow-band fluorescent-light image and a wide-band fluorescent-light image and a tissue-state image formed, is performed such that a luminosity V (brightness Z) is assigned to the computed-image and a tissue-state image is formed, which is combined with the tissue-form image to form a composite-image which is then displayed. The tissue-form image can be formed in the same way as in the first through the fourth embodiments, that is, by assigning a luminosity V (brightness Z) to the reflected-light image and forming a tissue-form image. When the composite-image formed according to the current embodiment represents three colors, the composite-image is displayed in the range color indicated by the thick arrow mark in FIG. 12. That is to say, when the hue is green (an appropriate hue can be used), for example: a normal tissue in a target that is located at a close distance from the stimulating-light emitting end of the endoscope insertion portion 100 will be displayed as a bright green; when said distance is far, a normal tissue is displayed as a dark green; a diseased tissue is displayed as a dark green when said distance is close; and a diseased tissue is displayed as a dark green when said distance is far. Other structures and operations are the same as those of the first through the fourth embodiments.

Next, a sixth embodiment of a fluorescent endoscope apparatus implementing the fluorescent-light image display apparatus according to the present invention will be explained. FIG. 13 is a schematic drawing of a fluorescent endoscope apparatus implementing the fluorescent-light image display apparatus according to the present invention. Note that the elements of the current embodiment shared in common with the fourth embodiment have been given the same reference numbers, and in so far as it is not particularly required, further explanation thereof has been omitted.

According to the fluorescent endoscope apparatus of the current embodiment, the light reflected from a target area upon irradiation thereof by an area-order light (R light Lr, G light Lg, and B light Lb) is obtained as a normal-image by the CCD photographing element 156 and displayed on the monitor 161, on the other hand, a wide-band fluorescent-light image based on the fluorescent-light emitted from a target area upon irradiation thereof by the stimulating-light is obtained by the CCD photographing element 156. Using the R-light as a reference-light, the reflected-light L7 reflected from a target area 50 upon irradiation thereof by the R-light is obtained as an IR reflected-light image. A computed-image is computed based on the division value between the wide-band fluorescent-light image and the IR reflected-light image, and a hue H is assigned based on the pixel values of the computed-image and a tissue-state image is formed. A saturation S and a luminosity V are assigned based on the brightness of the pixel values of the IR reflected-light image and a tissue-form image is formed, and a composite-image based on the tissue-state image and the tissue-form image is displayed on the monitor 162.

The fluorescent endoscope apparatus according to the sixth embodiment comprises a CCD photographing element 156 disposed a the stimulating-light emitting end thereof, an endoscope insertion portion to be inserted into a patient's body where the primary nidus and areas of suspected secondary infection are located, an illuminating unit 370 for emitting normal-image obtaining-use illuminating light and reference light, which is area-order color (Lr, Lg, Lb), and fluorescent-light image obtaining-use stimulating-light L2, a composite-image forming unit 380 for computing a division value between aforementioned wide-band fluorescent-light image and an IR reflected-light image, assigning a chromaticity (hue and saturation) to a computed-image based on said division value and forming a tissue-state image, for assigning a saturation and a luminosity to the pixel values of the IR reflected-light image and forming a tissue-form image, and for combining the tissue-state image and the tissue-form image to form a composite-image; an image processing unit 340 for performing image processing in order to display the normal-image and the composite-image as visible images; a control computer 360 connected to each unit and controlling the operation timing thereof; a monitor 161 for displaying as a visible image the normal-image processed by the image processing unit 340; and a monitor 162 for displaying as a visible image the composite-image processed by the image processing unit 340.

The light guide 351 is an integrated cable containing a light guide 351a for the area-order guide, and a stimulating-light use light guide 352b bundled together, and each of said light guides is connected to the illuminating unit 370.

The illuminating unit 370 comprises a white-light source 111 for emitting white-light and a white-light source use power source 112 electrically connected to said white-light source 111, a switching filter 314 for switching in order the separate the white-light into R-light, G-light, B-light, a filter rotating portion 315 for rotating the switching filter 314, and a GaN type semiconductor laser 211 for emitting fluorescent-light image obtaining-use stimulating-light L2 and a semiconductor-laser use power source 212 electrically connected to said GaN semiconductor laser 211.

The composite-image forming unit 380 comprises: an A/D converting circuit 381 for digitizing the image signal obtained by the CCD photographing element 156 when a target area is irradiated by stimulating-light L2 or R-light Lr; and image memory 382 composed of different memory zones for storing a wide-band fluorescent-light image and an IR reflected-light image; a tissue-state image forming means 383 for computing a division value between a wide-band fluorescent-light image and an IR reflected-light image memory 382, assigning a hue H to the computed value of each pixel and forming a tissue-state image; a tissue-form image forming means 385 for assigning a saturation and a luminosity to each to each pixel value of the IR reflected-light image stored in the image memory 382 and forming a tissue-form image; and a composite-image forming means 384 for combining the tissue-state image output from the tissue-state image forming means 383 and the tissue-form image output from the tissue-form image forming means 385 to form a composite-image.

The image processing unit 340 is provided with an A/D converting circuit 342 for digitizing the image signal obtained by the CCD photographing element 156 when the stimulating-light L2 or R-light Lr is emitted, a normal-image memory 343 for storing each color of a digitized normal-image, a video signal processing circuit 344 for converting to a video signal the three-color image signals of matched phases read out from said normal-image memory 343 when a normal-image is to be displayed and outputting said video signal, and also for converting to a video signal the composite-image output from the composite-image forming unit 380 when a fluorescent-light image is to be displayed and outputting said video signal.

Next, the operation of the fluorescent endoscope apparatus according to the current embodiment will be explained. According to the fluorescent endoscope apparatus of the current embodiment, the obtaining of a normal-image and the obtaining of a fluorescent-light image are performed in a time division manner, and an IR reflected-light image is obtained at the same time that the R-light occurring when a normal-image is obtained is emitted. A normal-image based on a normal-image is displayed on the monitor 161, and a composite-image based on a fluorescent-light image and an IR reflected-light image is displayed on the monitor 162. Because each image is obtained in a time division manner, the R-light Lr, G-light LG, B-light Lb and stimulating-light L2 are emitted in order.

First, the operation occurring when a normal-image is to be displayed will be explained. The reflected-light L7 of the R-light reflected from a target area 50 upon irradiation thereof by R-light is focused on the CCD photographing element 156 as a R-light reflected-light image. The R image signal photoelectrically converted by the CCD photographing element 156 is digitized by the A/D converting circuit 342 and stored in the R image memory zone of the image memory 343. Subsequently, a G image signal and a B image signal are obtained by the same operation, and said image signal are each stored in a G image signal memory zone and a B image signal memory zone, respectively, of the image memory 343. Further, the R image signal is also used as an IR reflected-light image, and after being digitized by the A/D converting circuit 381, it is stored in the IR reflected-image memory zone of the image memory 382.

When the three color image signals are stored in the image memory 343, the display timing thereof is matched and they are readout simultaneously, converted to video signals by the video signal processing circuit 344, output to the monitor 161, and displayed thereon as a color image.

Next, the operation wherein a fluorescent-light image and an IR reflected-light image are obtained, and a composite-image is formed based on both of said images and displayed will be explained. When obtaining a fluorescent-light image, based on a signal from the control computer 360, the semiconductor-laser use power source 212 is activated and stimulating-light L2 having a wavelength of 410 nm is emitted from the GaN-type semiconductor laser 211. The stimulating-light L2 is transmitted by a lens 213 and enters the stimulating-light use light guide 351*b*, and after being guided to the stimulating-light emitting end of the endoscope insertion portion, the stimulating-light L2 is projected onto a target area 50 by an illuminating lens 154.

The fluorescent-light emitted from the target area upon irradiation thereof by the stimulating-light L2 is focused by a focusing lens 155, reflected by a prism 157, transmitted by the mosaic filter 354 and focused on the CCD photographing element 156 as a fluorescent-light image. Because the reflected stimulating-light L2 occurring at this time is cutoff by a stimulating-light cutoff filter 355, it does not enter the CCD photographing element 156.

The image signal photoelectrically converted by the CCD photographing element 156 is digitized by the A/D converting circuit 381 of the composite-image forming means 380 and stored in the wide-band fluorescent-light image memory zone of the image memory 382.

On the other hand, the IR reflected-light image obtained when the normal-image is obtained has already been stored in the image memory 382.

Regarding the wide-band fluorescent-light image and the IR reflected-light image stored in the image memory 382, the tissue-state image forming means 383 divides each pixel value of the wide-band fluorescent-light image by the corresponding pixel value of the IR reflected-light image, and using the division value obtained thereby and a pre-recorded lookup-table, assigns a hue H occurring in the Munsell color specification system and forms a tissue-state image, and outputs said tissue-state image to the composite-image forming means 380.

The composite-image forming means 380 combines the tissue-state image and the tissue-form image based on the luminosity V and saturation S to form a composite-image. Note that when the composite image is to be displayed as a color image, RGB conversion is performed and a composite-image is formed and output to the video signal converting circuit 344.

The composite-image converted to a video signal by the video signal converting circuit 344 is input to the monitor 170, and displayed on said monitor as a visual image. The continuous operation described above is controlled by the control computer 360.

Figure 7:
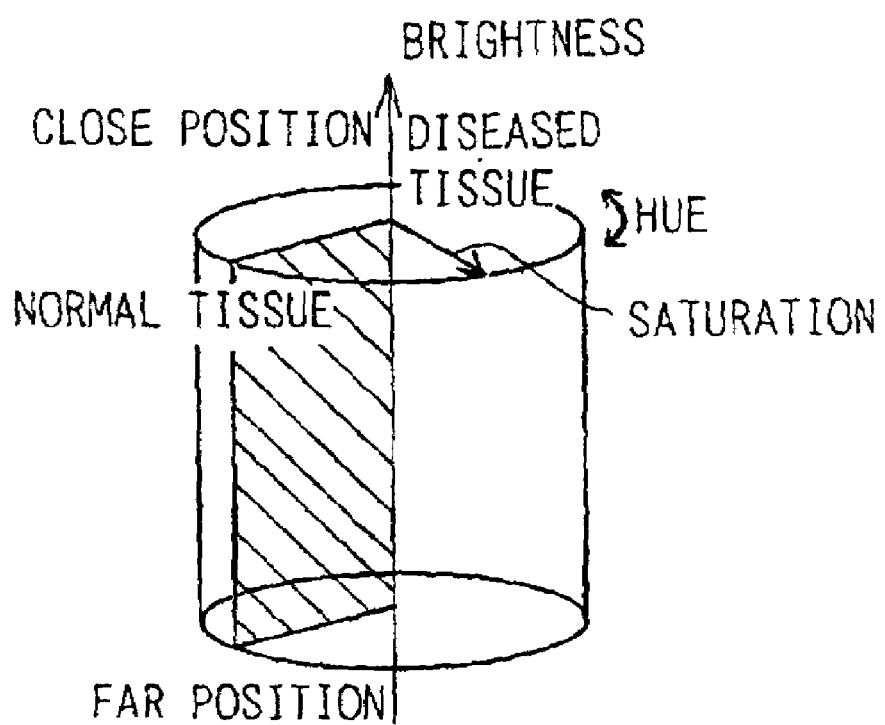
FIG. 7 shows the color range of a composite-image displayed by a fluorescent endoscope apparatus according to the third embodiment of the present invention.

When the composite-image formed according to the current embodiment is represented by three color attributes thereof, the image is displayed in the colors of the range show in the perspective view of FIG. 7. That is to say, for example: when the stimulating-light emitting end of the endoscope insertion portion is located at a position in which the distance from to the target area is close, a normal tissue is displayed as a bright, vivid green; a normal tissue located at a position wherein said distance is far is displayed as a dark, toneless green; a diseased tissue located at a position wherein said distance is close is displayed as a bright, dark red; and a diseased tissue located at a position wherein said distance is far is displayed as a dark, toneless red.

Next, a seventh embodiment of a fluorescent endoscope apparatus implementing the fluorescent-light image display apparatus according to the present invention will be explained. According to the current embodiment, the forming of a tissue-state image occurring in the sixth embodiment, wherein a computed-image is computed based on the division value between the wide-band fluorescent-light image and the IR reflected-light image, a hue H is assigned based on the pixel values of the computed-image and a tissue-state image is formed, is performed such that a hue and a saturation are assigned to the computed-image and a tissue-state image formed, which is combined with the tissue-form image to form a composite-image which is then displayed. When the composite-image formed according to the current embodiment is represented by points in an HSV color space, the composite-image is displayed in the range of color shown by the perspective view in FIG. 12. That is to say, for example: when the stimulating-light emitting end of the endoscope insertion portion is located at a position in which the distance from to the target area is close, a normal tissue is displayed as a bright, vivid green; a normal tissue located at a position wherein said distance is far is displayed as a dark, toneless green; a diseased tissue located at a position wherein said distance is close is displayed as a bright, dark red; and a diseased tissue located at a position wherein said distance is far is displayed as a dark, toneless red. Other structures and operations are the same as those of the sixth embodiment.

Next, a eighth embodiment of a fluorescent endoscope apparatus implementing the fluorescent-light image display apparatus according to the present invention will be explained. According to the current embodiment, the forming of a tissue-form image occurring in the sixth embodiment, wherein a saturation S and a luminosity V are assigned to the IR reflected-light image and a tissue-form image is formed, is performed such that only a saturation S is assigned to the IR reflected-light image and a tissue-form image is formed, which is combined with the tissue-state image to form a composite-image which is then displayed. When the composite-image formed according to the current embodiment is represented by three color attributes thereof, the composite-image is displayed in the color range indicated by the perspective view in FIG. 16. That is to say, when the luminosity is 100% (an appropriate luminosity can be used), for example: a normal tissue in a target that is located at a close distance from the stimulating-light emitting end of the endoscope insertion portion 100 will be displayed as a vivid green; when said distance is far, a normal tissue is displayed as a toneless green; a diseased tissue is displayed as a vivid red when said distance is close; and a diseased tissue is displayed as a toneless red when said distance is far. Other structures and operations are the same as those of the sixth embodiment.

Figure 17:
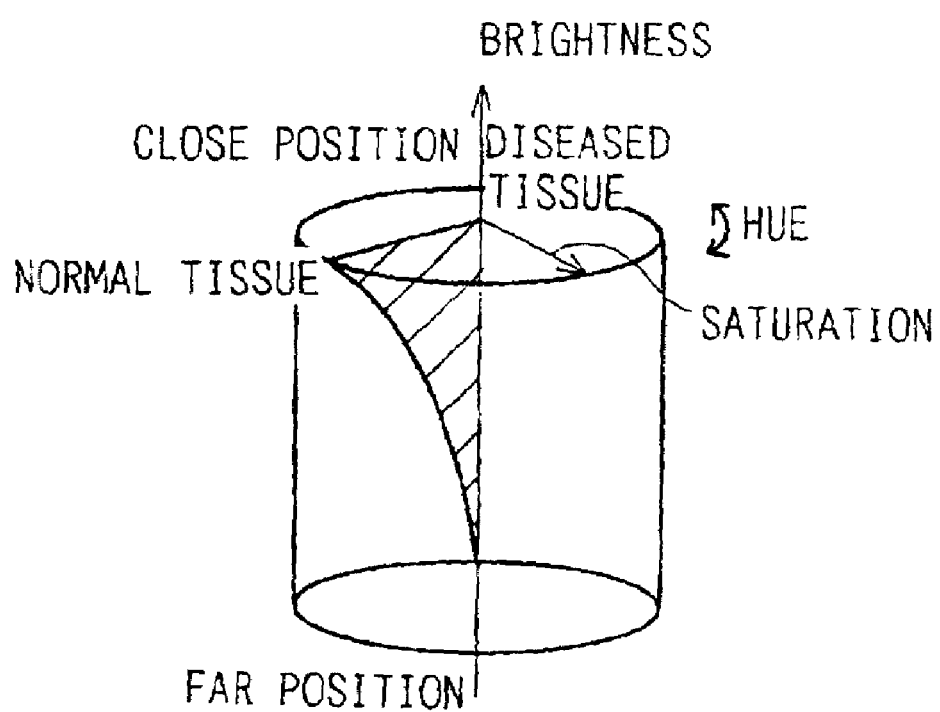
FIG. 17 shows the color range of a composite-image displayed by a fluorescent endoscope apparatus according to another embodiments of the present invention.

In addition, aside from the assigning of a color data, etc. to the tissue-state image and the assigning of a color data, etc. to the tissue-form image occurring in each of the embodiments described above, it is also feasible to assign a saturation to a tissue-state image, and to assign a saturation and a luminosity to a tissue-form image. In this case, a composite-image based on a tissue-state image and a tissue-form image is displayed in the color range shown in the perspective view of FIG. 17. That is to say, for example: when the hue is green (an appropriate hue can be used): for a normal tissue located at a position in which the distance from the stimulating-light emitting end of the endoscope insertion portion to the target area is close, the green is displayed bright and vivid; for a normal tissue locate data position wherein said distance is far, the green is displayed dark and vivid; for a diseased tissue located at a position wherein said distance is close, the toneless bright white is displayed; and for a diseased tissue located at a position wherein said distance is far, the toneless black is displayed. In this case, the image is displayed in colors in which darkness is more emphasized than in the color range shown in the perspective view of FIG. 7 used in the third embodiment. Further, for cases such as that described above, in which a saturation is assigned to both the tissue-state image and the tissue-form image, a predetermined function f can be determined to assign the saturation such that saturation=f (tissue-state image, tissue-form image). The predetermined function f, can be, for example, f (tissue-state image, tissue-form image)=tissue-state image×tissue-form image.

Figure 18:
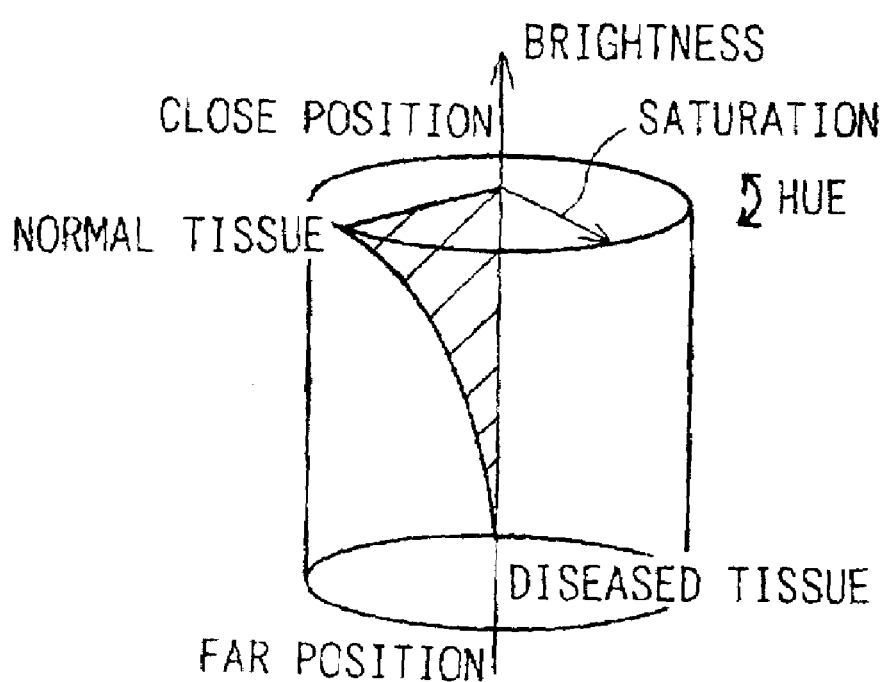
FIG. 18 shows the color range of a composite-image displayed by a fluorescent endoscope apparatus according to another embodiments of the present invention.
Figure 19:
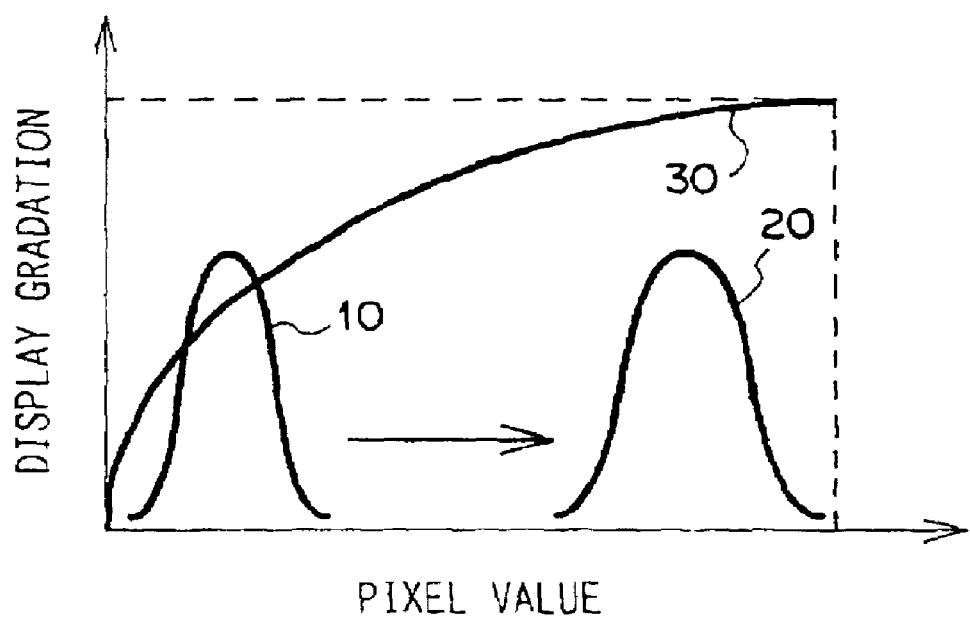
FIG. 19 is a graph provided for explanation of the operation for assigning a display gradation of the brightness data of an IR reflected-light image that has been multiplied by a predetermined coefficient.
Figure 21:
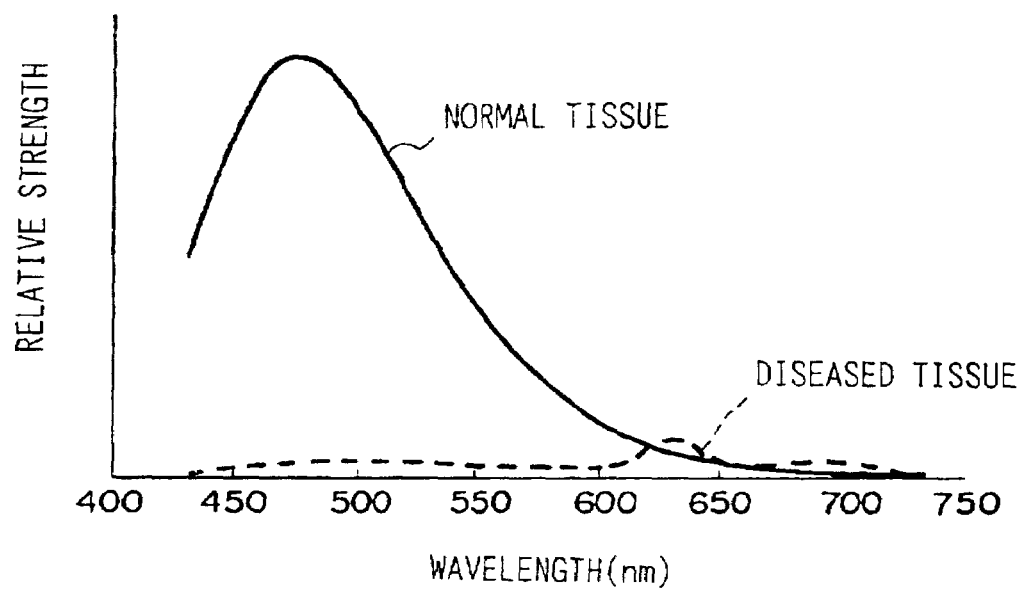
FIG. 21 is a graph provided for explanation of the strength distribution of the fluorescent spectra of a normal tissue and of a diseased tissue.

In addition, for example, a luminosity can be assigned to the tissue-state image and a luminosity and a saturation can be assigned to the tissue-form image. In this case, when a composite-image based on a tissue-state image and a tissue-form image, the composite-image is displayed in the color range shown in the perspective view of FIG. 18. That is to say, for example: when the hue is green (an appropriate hue can be used): for a normal tissue located at a position in which the distance from the stimulating-light emitting end of the endoscope insertion portion to the target area is close, the green displayed is bright; for a normal tissue located at a position wherein said distance is relatively far, the green displayed is toneless and dark; for a diseased tissue located at a position wherein said distance is close, the green displayed is dark; and for a diseased tissue located at a position wherein said distance is relatively far, the green displayed is toneless and dark (darker than the darkness of aforementioned green displayed for a normal tissue when said distance is far).

Further, according to each of the embodiments described above, when a tissue-form image is formed, an IR reflected-light image has been used; however, it is also feasible that a fluorescent-light image be used to form a tissue-form image. In this case, although the IR reflected-light image is the true tissue-form, that is, the IR reflected-light image reflects the data relating to the distance between the stimulating-light emitting end of the endoscope insertion portion and the target area, the fluorescent-light image reflects not only said distance data, but also the tissue-state data. Therefore, for cases in which a hue is assigned to a tissue-state image and brightness (luminosity) based on the fluorescent-light image is assigned to a tissue-form image and a composite-image is formed based on both the tissue-state image and the tissue-form image, because the green by which a normal tissue is displayed is even brighter and the red by which a diseased tissue is displayed is even darker in such a composite-image, a normal tissue can be accurately distinguished from a diseased tissue.

Still further, according to each of the embodiments described above, for cases in which there is color data and brightness data that is not yet assigned to a tissue-state or a tissue-form image, it is desirable to setup a configuration enabling manual adjustment. In particular, it is even more desirable that such a configuration is adopted for cases in which a hue, which is one of the color data, is not assigned.

Additionally, according to each of the embodiments described above, a hue and a saturation of a color appearance system is used as the color data; however, it is also feasible that a chromaticity (XY) of a color mixing system, or a color difference of a visible image signal (such as the IQ of the YIQ of an NTSC signal, etc.) can be used as the color data.

Further, a charge-multiplying type CCD photographing element can be used as the CCD photographing element occurring in the embodiments described above. A charge-multiplying type CCD photographing element is called a CMD (Charge Multiplying Detector) -CCD, and multiplies the signal charge by a charge multiplying effect occurring due to the ionization brought about by causing atoms and conductive electrons to collide in a strong electrical field; providing for increased sensitivity of the photographing element.

Still further, according to each of the embodiments described above, the method of displaying a normal-image and a composite-image is such that a separate monitor is used to display each of the two types of image, however, a single multi-purpose monitor can be used to display both types of images. Here, the switching of the normal-image and the composite-image can be performed automatically by the control computer, or the operator can perform the switching at will by use of an appropriate switching means.

In addition, according to each of the embodiments described above, the image fiber can be a composite glass fiber instead of a silicon fiber. Here, because fluorescent light is emitted when stimulating-light enters a composite glass fiber, it is necessary to dispose a stimulating-light cutoff filter between the focusing lens and the fluorescent-light image input end of the image fiber. By changing the image fiber from a silicon fiber to a composite glass fiber, the cost can be reduced.

Further, according to the first through the third embodiments, a configuration is adopted in which a normal-image use CCD photographing element is provided at the forward end of the endoscope insertion portion, however, by making use of an image fiber, the CCD photographing element can be provided within the photographing unit. Also, the normal-image use image fiber, the fluorescent-light image and reflected-light image fiber and the photographing element can be made into a multi-purpose configuration. In this case, using a switching filter divided into four portions or a four section mosaic filter, etc., a filtering means for use in obtaining a normal-image can be provided on the front face of the photographing element.

Still further, according to each of the embodiments described above, the processing relating to displaying a composite-image is not limited to being performed on each pixel unit; it can be performed on a desired n×m pixel unit as per the needs of an operator.

Additionally, for cases in which there are regions for which the processing relating to the displaying of a composite-image has not been performed, by displaying those regions in a predetermined display color, the regions which have been subjected to the processing relating to the displaying of a composite-image can be clearly displayed. For cases in which only those pixels selected with predetermined intervals are subjected to said processing, etc., a gap-compensated displaying can be performed by use of the processing result of the adjacent pixels.

Further, any stimulating-light source emitting stimulating-light having a wavelength within the 400-420 nm wavelength band can be selected as the stimulating-light source.

Still further, separate light sources have been used for the stimulating-light source and the white-light source, however, by use of an appropriate switching filter, the light source can be made into a multi-purpose light source.

What is claimed is:

1. A fluorescent-light image display method comprising:
   obtaining a fluorescent-light image based on the strength of fluorescent-light emitted from a target area upon irradiation thereof by a stimulating-light,
   assigning at least one of color data and brightness data to a computed-image based on said fluorescent-light image and forming a tissue-state image representing mainly the state of the tissue in the target area,
   assigning to said fluorescent-light image at least one of color data and brightness data corresponding to the at least one of color data and the brightness data assigned to said tissue-state image and forming a tissue-form image representing mainly the form of the tissue in the target area, such that said tissue-state image and said tissue-form image are initially separate images,
   combining the tissue-state image and the tissue-form image to form a composite-image, and
   displaying the composite-image,
   wherein the brightness data is a degree of brightness according to a color mixing system or a color appearance system, each being one of color specification systems, or luminance according to an image signal system.

2. A fluorescent-light image display method as defined in claim 1, wherein the computed-image is based on the ratio of one to another of two wavelength components among a plurality of wavelength components of said fluorescent-light image, each of said wavelength components representing a different wavelength band of fluorescent light.

3. A fluorescent-light image display method as defined in claim 1, further comprising computing a statistical quantity of the pixel values of one of the obtained images and assigning display gradation of the brightness data based on said statistical quantity.

4. A fluorescent-light image display method as defined in claim 3, wherein the statistical quantity is computed from a desired portion of said one of the obtained images.

5. A fluorescent-light image display method as defined in claim 3, further comprising,
   computing a coefficient based on the statistical quantity,
   multiplying said one of the obtained images by said computed coefficient, and
   assigning said display gradation of the brightness data to said one of the obtained images that has been multiplied by the coefficient.

6. A fluorescent-light image display method as defined in claim 3, further comprising,
   determining a gradation processing function representing the display gradation of the brightness data based on the statistical quantity, and
   assigning the display gradation of the brightness data, based on the determined gradation processing function, to said one of the obtained images.

7. A fluorescent-light image display method as defined in claim 1, wherein the color data is a chromaticity occurring in a color mixing system or a color appearance system, each being one of color specification systems.

8. A fluorescent-light image display method comprising:
   obtaining a fluorescent-light image based on strength of fluorescent-light emitted from a target area upon irradiation thereof by a stimulating-light,
   obtaining a reflected-light image based on strength of reflected-light reflected from the target area upon irradiation thereof by a reference light,
   assigning at least one of color data and brightness data to a computed-image based on said fluorescent-light image and forming a tissue-state image representing mainly the state of the tissue in the target area,
   assigning to said reflected-light image at least one of color data and brightness data corresponding to the at least one of color data and the brightness data assigned to said tissue-state image and forming a tissue-form image representing mainly the form of the tissue in the target area, such that said tissue-state image and said tissue-form image are initially separate images,
   combining the tissue-state image and the tissue-form image to form a composite-image, and
   displaying the composite-image,
   wherein the brightness data is a degree of brightness according to a color mixing system or a color appearance system, each being of color specification systems, or luminance according to an image signal system.

9. A fluorescent-light image display method as defined in claim 8, wherein the computed-image is based on the ratio of one to another of two wavelength components among a plurality of wavelength components of said fluorescent-light image, each of said wavelength components representing a different wavelength band of fluorescent light.

10. A fluorescent-light image display method as defined in claim 8, wherein the computed-image is based on ratio between said fluorescent-light image and said reflected-light image.

11. A fluorescent-light image display method as defined in claim 8, further comprising computing a statistical quantity of the pixel values of one of the obtained images and assigning display gradation of the brightness data based on said statistical quantity.

12. A fluorescent-light image display method as defined in claim 11, wherein the statistical quantity is computed from a desired portion of said one of the obtained images.

13. A fluorescent-light image display method as defined in claim 11, further comprising
computing a coefficient based on the statistical quantity, multiplying said one of the obtained images by said computed coefficient, and assigning said display gradation of the brightness data to said one of the obtained images that has been multiplied by the coefficient.

14. A fluorescent-light image display method as defined in claim 11, further comprising,
determining a gradation processing function representing the display gradation of the brightness data based on the statistical quantity, and
assigning the display gradation of the brightness data, based on the determined gradation processing function, to said one of the obtained images.

15. A fluorescent-light image display method as defined in claim 8, wherein the color data is a chromaticity occurring in a color mixing system or a color appearance system, each being one of color specification systems.

16. A fluorescent-light image display apparatus comprising:
fluorescent-light image obtaining means for obtaining a fluorescent-light image based on the strength of fluorescent light emitted from a target area upon irradiation thereof by a stimulating-light,
tissue-state image forming means for assigning at least one of color data and brightness data to a computed-image based on said fluorescent-light image and forming a tissue-state image representing mainly the state of the tissue in the target area,
tissue-form image forming means for assigning to said fluorescent-light image at least one of color data and brightness data corresponding to the at least one of color data and the brightness data assigned to said tissue-state image and forming a tissue-form image representing mainly the form of the tissue in the target area, such that said tissue-state image and said tissue-form image are initially separate images,
composite-image forming means for combining the tissue-state image and the tissue-form image to form a composite-image, and
display means for displaying the composite-image formed by said composite-image forming means,
wherein the brightness data is a degree of brightness according to a color mixing system or a color appearance system, each being of color specification systems, or luminance according to an image signal system.

17. A fluorescent-light image display apparatus as defined in claim 16, wherein the computed-image is based on the ratio of one to another of two wavelength components among a plurality of wavelength components of said fluorescent-light image, each of said wavelength components representing a different wavelength band of fluorescent light.

18. A fluorescent-light image display apparatus as defined in claim 16, further comprising:
statistical-quantity computing means for computing a statistical quantity of the pixel values of one of the obtained images, and
gradation processing means for assigning display gradation of the brightness data based on said statistical quantity.

19. A fluorescent-light image display apparatus as defined in claim 18, wherein said statistical-quantity computing means computes the statistical quantity from a desired portion of said one of the obtained images.

20. A fluorescent-light image display apparatus as defined in claim 18, wherein said gradation processing means computes a coefficient based on the statistical quantity, multiplies said one of the obtained images by said computed coefficient, and assigns said display gradation of the brightness data to said one of the obtained images that has been multiplied by the coefficient.

21. A fluorescent-light image display apparatus as defined in claim 18, wherein said gradation processing means determines a gradation processing function representing the display gradation of the brightness data based on the statistical quantity, and assigns the display gradation of the brightness data, based on said determined gradation processing function, to said one of the obtained images.

22. A fluorescent-light image display apparatus as defined in claim 18, further comprising bit-shifting means for bit-shifting the pixel values of said one of the obtained images when each of said pixel values is represented by data of 9 bits or more, so that each of said pixel values is represented by data of 8 bits or less,
wherein said statistical-quantity computing means computes the statistical quantity based on said bit-shifted data.

23. A fluorescent-light image display apparatus as defined in claim 18, wherein the gradation processing means is capable of being turned ON and OFF.

24. A fluorescent-light image display apparatus as defined in claim 18, wherein said statistical quantity is a combination of a plurality of values including an average of the pixel values or the largest pixel value.

25. A fluorescent-light image display apparatus as defined in claim 16, wherein the color data is a chromaticity occurring in a color mixing system or a color appearance system, each being one of color specification systems.

26. A fluorescent-light image display apparatus as defined in claim 16, wherein when combining the tissue-state image and the tissue-form image to form the composite-image, for cases in which the number of pixels of the two images differ, the composite-image forming means converts the number of pixels of each image to the number of pixels of one of either of the two images before forming the composite-image.

27. A fluorescent-light image display apparatus as defined in claim 16, wherein said fluorescent-light image display apparatus is provided in a form of an endoscope provided with an insertion portion to be inserted into a living body.

28. A fluorescent-light image display apparatus as defined in claim 16, wherein a light source of the stimulating-light is a GaN type semiconductor laser, and the wavelength band of the stimulating-light is within the 400-420 nm wavelength range.

29. A fluorescent-light image display apparatus comprising:
  fluorescent-light image obtaining means for obtaining a fluorescent-light image based on strength of the fluorescent light emitted from a target area upon irradiation thereof by a stimulating-light,
  reflected-light image obtaining means for obtaining a reflected-light image based on strength of the reflected-light reflected from the target area upon irradiation thereof by a reference light,
  tissue-state forming means for assigning at least one of color data and brightness data to a computed-image based on said fluorescent-light image and forming a tissue-state image representing mainly the state of the tissue in the target area,
  tissue-form image forming means for assigning to said reflected-light image at least one of color data and brightness data corresponding to the at least one of color data and the brightness data assigned to said tissue-state image and forming a tissue-form image representing mainly the form of the tissue in the target area, such that said tissue-state image and said tissue-form image are initially separate images,
  composite-image forming means for combining the tissue-state image and the tissue-form image to form a composite-image, and
  display means for displaying the composite-image formed by said composite-image forming means,
  wherein the brightness data is a degree of brightness according to a color mixing system or a color appearance system, each being of color specification systems, or luminance according to an image signal system.

30. A fluorescent-light image display apparatus as defined in claim 29, wherein the computed-image is based on the ratio of one to another of two wavelength components among a plurality of wavelength components of said fluorescent-light image, each of said wavelength components representing a different wavelength band of fluorescent light.

31. A fluorescent-light image display apparatus as defined in claim 29, wherein the computed-image is based on ratio between said fluorescent-light image and said reflected-light image.

32. A fluorescent-light image display apparatus as defined in claim 29, further comprising
  statistical-quantity computing means for computing a statistical quantity of the pixel values of one of the obtained images, and
  gradation processing means for assigning display gradation of the brightness data based on said statistical quantity.

33. A fluorescent-light image display apparatus as defined in claim 32, wherein said statistical-quantity computing means computes the statistical quantity from a desired portion of said one of the obtained images.

34. A fluorescent-light image display apparatus as defined in claim 32, wherein said gradation processing means computes a coefficient based on the statistical quantity, multiplies said one of the obtained images by said computed coefficient, and assigns said display gradation of the brightness data to said one of the obtained images that has been multiplied by the coefficient.

35. A fluorescent-light image display apparatus as defined in claim 32, wherein said gradation processing means determines a gradation processing function representing the display gradation of the brightness data based on the statistical quantity, and assigns the display gradation of the brightness data, based on said determined gradation processing function, to said one of the obtained images.

36. A fluorescent-light image display apparatus as defined in claim 32, further comprising a bit-shifting means for bit-shifting the pixel values of said one of the obtained images when each of said pixel values is represented by data of 9 bits or more, so that each of said pixel values is represented by data of 8 bits or less,
  wherein said statistical-quantity computing means computes the statistical quantity based on said bit-shifted data.

37. A fluorescent-light image display apparatus as defined in claim 32, wherein the gradation processing means is capable of being turned ON and OFF.

38. A fluorescent-light image display apparatus as defined in claim 32, wherein said statistical quantity is a combination of a plurality of values including an average of the pixel values or the largest pixel value.

39. A fluorescent-light image display apparatus as defined in claim 29, wherein the color data is a chromaticity occurring in a color mixing system or a color appearance system, each being one of color specification systems.

40. A fluorescent-light image display apparatus as defined in claim 29, wherein when combining the tissue-state image and the tissue-form image to form the composite-image, for cases in which the number of pixels of the two images differ, the composite-image forming means converts the number of pixels of each image to the number of pixels of one of either of the two images before forming the composite-image.

41. A fluorescent-light image display apparatus as defined in claim 29, wherein said fluorescent-light image display apparatus is provided in a form of an endoscope provided with an insertion portion to be inserted into a living body.

42. A fluorescent-light image display apparatus as defined in claim 29, wherein a light source of the stimulating-light is a GaN type semiconductor laser, and the wavelength band of the stimulating-light is within the 400-420 nm wavelength range.

* * * * *